(12) United States Patent
Upadhyay

(10) Patent No.: US 12,134,601 B2
(45) Date of Patent: Nov. 5, 2024

(54) COMPOUNDS FOR INHIBITING LY6K AND METHODS OF USING SAME

(71) Applicant: The Henry M. Jackson Foundation for the Advancement of Military Medicine, Inc., Bethesda, MD (US)

(72) Inventor: Geeta Upadhyay, Washington, DC (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 616 days.

(21) Appl. No.: 16/762,424

(22) PCT Filed: Nov. 9, 2018

(86) PCT No.: PCT/US2018/060121
§ 371 (c)(1),
(2) Date: May 7, 2020

(87) PCT Pub. No.: WO2019/094788
PCT Pub. Date: May 16, 2019

(65) Prior Publication Data
US 2021/0009522 A1 Jan. 14, 2021

Related U.S. Application Data

(60) Provisional application No. 62/583,998, filed on Nov. 9, 2017.

(51) Int. Cl.
*C07D 219/10* (2006.01)
*C07C 39/15* (2006.01)

(52) U.S. Cl.
CPC ............ *C07D 219/10* (2013.01); *C07C 39/15* (2013.01)

(58) Field of Classification Search
None
See application file for complete search history.

(56) References Cited

U.S. PATENT DOCUMENTS

| | | | |
|---|---|---|---|
| 4,258,191 A | 3/1981 | Dubicki et al. | |
| 4,399,283 A | 8/1983 | Fisher et al. | |
| 2004/0180812 A1* | 9/2004 | Dicker | A61K 41/0038 514/13.8 |
| 2004/0188812 A1 | 9/2004 | Koschmieder et al. | |
| 2006/0093553 A1* | 5/2006 | Dang | A61P 35/00 514/19.5 |
| 2006/0111389 A1 | 5/2006 | Neidle et al. | |
| 2017/0022166 A1 | 1/2017 | Wald et al. | |

FOREIGN PATENT DOCUMENTS

| | | |
|---|---|---|
| EP | 0035862 A2 | 9/1981 |
| KR | 2016107477 A | 9/2016 |
| WO | WO 2010/019680 A1 | 2/2010 |
| WO | WO 2016/140552 | 9/2016 |
| WO | WO2018222134 | * 12/2018 |

OTHER PUBLICATIONS

AlHosiny et al., Ly6E/K Signaling to TGFβ Promotes Breast Cancer Progression, Immune Escape, and Drug Resistance. Cancer Research, 2016, 76, 3376-3386.*
International Search Report and Written Opinion for International Application No. PCT/US2018/060121 dated Feb. 21, 2019. (10 pages).
Ambrish Roy et al. "PoLi: A Virtual Screening Pipeline Based on Template Poket and Ligand Similarity", Journal of Chemical Information and Modeling, 2015, vol. 55, pp. 1757-1770.
Jeffrey L. Jurlina et al. "Redox Chemistry of the 9-Anilinoacridine Class of Antitumor Agents", J.Med. Chem., 1987, vol. 30, No. 3, pp. 473-480.
Midrar A. Hossiny et al. "Ly6E/K signaling to TGF-β promotes breast cancer progression, immune escape and drug resistance". Cancer Res Published OnlineFirst Apr. 11, 2016, pp. 2, 9-13.
William A. Denny et al. "Potential Antitumor Agents. 36. Quantitative Relationships between Experimental Antitumor Activity, Toxicity, and Structure for the General Class of 9-Anilinoacridine Antitumor Agents", J.Med. Chem., 1982, vol. 25, No. 3, pp. 276-315.
William A. Denny et al. "Potential Antitumor Agents. 40. Orally Active 4,5-Disubstituted Derivatives of Amsacrine", J. Med. Chem., 1984, vol. 27, No. 3, pp. 363-367.
Denny, et al. Potential antitumor agents. 32. Role of agent base strength in the quantitative structure-antitumor relationships for 4'-(9-acridinylamino)methanesulfonanilide analogs. J. Med. Chem. 1979, 22, 12, 1453-1460.
European Search Report & Opinion dated Oct. 28, 2021 for EP Application No. 18875928.6. 12 pages.
Klopman, et al. Computer-automated structure evaluation of antileukemic 9-anilinoacridines. Molecular Pharmacology, 1987, 31(4), 457-476.
Kumar, et al. Small molecule binders of Ly6K inhibit tumorigenic growth and induce immunity via TGFb/Stat1 and PDL1 pathway. Journal for ImmunoTherapy of Cancer 2017, 5(Suppl 2):p. 93.
Mezencev, et al. Identification of inhibitors of ovarian cancer stem-like cells by high-throughput screening. Journal of Ovarian Research 2012, 5:30.

* cited by examiner

*Primary Examiner* — Po-Chih Chen
(74) *Attorney, Agent, or Firm* — Sheppard Mullin Richter & Hampton LLP

(57) ABSTRACT

The present technology relates to compounds that inhibit human Ly6K and homologs thereof. Also disclosed are methods of using such compounds to: inhibit activity of a Ly6K protein in a cell; decrease migration, colony formation, and/or proliferation of a cell; modulate expression of a gene in a cell, reduce suppression of the immune response to cancer in a subject, decrease tumorigenic growth of a cancer in a subject, and treat or prevent in a subject a disorder mediated by Ly6K protein.

8 Claims, 15 Drawing Sheets

NSC243928

NSC11150

COMPOUNDS FOR INHIBITING LY6K AND METHODS OF USING SAME

This application is the U.S. national stage application of International Application No. PCT/US2018/060121, filed Nov. 9, 2018, which claims the benefit under 35 U.S.C. § 119(e) of U.S. Provisional Patent Application Ser. No. 62/583,998, filed Nov. 9, 2017, which is hereby incorporated by reference in its entirety.

This invention was made with government support under R01CA227694 and CA175862 awarded by the National Institutes of Health. The government has certain rights in the invention.

FIELD OF THE INVENTION

This technology relates to compounds that inhibit Ly6K, as well as methods of using such compounds.

BACKGROUND OF THE INVENTION

Triple negative breast cancer (TNBC) is a highly heterogeneous disease and composed of multiple subtypes[1]. TNBC patients suffer the worst outcome and have fewer therapeutic options compared to patients with estrogen receptor (ER) positive and human epidermal growth receptor 2 (Her 2) positive breast cancer[3].

Targeted therapies such as hormone therapy or anti-Her2 therapies do not work for TNBC[1]. Although immunotherapy has led to a paradigm shift in cancer therapeutics, its effect in TNBC has been modest[2]. TNBC affects younger women and has the worst overall survival rate among breast cancer subtypes[3]. There is an urgent need to identify and develop novel, effective and safe approaches to treat TNBC.

The immune checkpoint protein PD-L1 is increased in TNBC and its increased expression contributes to tumor immune escape[4,5]. TGFβ signaling represents another key hub in cancer that activates both immune and non-immune associated pathways of tumor progression[6,7]. The widespread expression and essential function of TGFβ signaling and PD-L1 in many normal tissues, however, make them problematic targets for therapeutic intervention.

The present technology is directed to overcoming these and other deficiencies in the art.

SUMMARY OF THE INVENTION

A first aspect of the present technology relates to a compound (or pharmaceutically acceptable salt, ester, enol ether, enol ester, solvate, or hydrate thereof) selected from the group consisting of:
(a) a compound of Formula I or salt thereof:

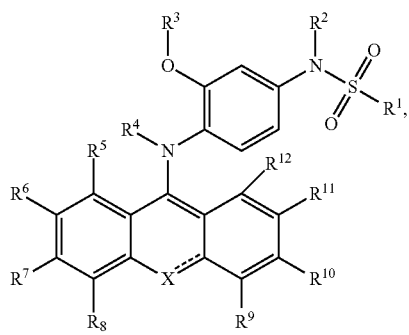

I wherein:
≡ is a single or double bond;

$R^1$ is selected from the group consisting of —$C_{1-8}$ alkyl, —$C_{3-8}$ cycloalkyl, aryl, heterocyclyl, heteroaryl, -phenylene-$NH_2$, and —$C_{1-4}$ alkylene-$NH_2$;

$R^2$ is selected from the group consisting of H, —$C_{1-3}$ alkyl, and —C(O)—$C_{1-5}$ alkyl;

$R^3$ is —$C_{1-6}$ alkyl or —$C_{1-3}$ alkylene-OH;

$R^4$ is H or —$C_{1-6}$ alkyl;

$R^5$ is selected from the group consisting of H, —$C_{1-3}$ alkyl, —$NO_2$, —O—$C_{1-3}$ alkyl, halogen, —$NR_2$, and —C(O)—OR, wherein each R is independently H or —$C_{1-4}$ alkyl;

$R^6$ is selected from the group consisting of H, —$C_{1-4}$ alkyl, —$NR_2$, —$NO_2$, —O—$C_{1-3}$ alkyl, halogen, and —C(O)—OR, wherein each R is independently H or —$C_{1-4}$ alkyl;

$R^7$ is selected from the group consisting of H, —$C_{1-4}$ alkyl, —$C_{1-3}$ alkylene-SH, —CN, —$CF_3$, —$NR_2$, —$NO_2$, —N=$N^+$=$N^-$, —NH—N=$N^+$—$C_{1-3}$ alkyl, —NH—C(O)—$C_{1-3}$ alkyl, —NH—C(O)—O—$C_{1-3}$ alkyl, —OR, —SR, —S—$C_{1-3}$ alkylene-SH, —S($O_2$)—$C_{1-3}$ alkyl, —NH—$SO_2$—$C_{1-3}$ alkyl, and halogen, wherein each R is independently H or —$C_{1-4}$ alkyl;

$R^8$ is selected from the group consisting of H, —$C_{1-3}$ alkyl, —$C_{1-3}$ alkylene-C(O)—$NH_2$, —CN, —C—$NR_2$, —O—$C_{1-3}$ alkyl, halogen, and phenyl, wherein each R is independently H or —$C_{1-4}$ alkyl;

$R^9$ is selected from the group consisting of H, —$C_{1-3}$ alkyl, —$C_{1-3}$ alkylene-C(O)—$NH_2$, —CN, —C—$NR_2$, —O—$C_{1-3}$ alkyl, halogen, and phenyl, wherein each R is independently H or —$C_{1-4}$ alkyl;

$R^{10}$ is selected from the group consisting of H, —$C_{1-4}$ alkyl, —$C_{1-3}$ alkylene-SH, —CN, —$CF_3$, —$NR_2$, —$NO_2$, —N=$N^+$=N, —NH—N=$N^+$—$C_{1-3}$ alkyl, —NH—C(O)—$C_{1-3}$ alkyl, —NH—C(O)—O—$C_{1-3}$ alkyl, —OR, —SR, —S—$C_{1-3}$ alkylene-SH, —S($O_2$)—$C_{1-3}$ alkyl, —NH—$SO_2$—$C_{1-3}$ alkyl, and halogen, wherein each R is independently H or $C_{1-4}$ alkyl;

$R^{11}$ is selected from the group consisting of H, —$C_{1-4}$ alkyl, —$NR_2$, —$NO_2$, —O—$C_{1-3}$ alkyl, halogen, and —C(O)—OR, wherein each R is independently H or $C_{1-4}$ alkyl;

$R^{12}$ is selected from the group consisting of H, —$C_{1-3}$ alkyl, —$NO_2$, —O—$C_{1-3}$ alkyl, halogen, —$NR_2$, and —C(O)—OR, wherein each R is independently H or $C_{1-4}$ alkyl; and X is selected from the group consisting of —C($R^{13}$, $R^{14}$)—, —N($R^{15}$)—, —O—, and —S—, wherein:
one of $R^{13}$ and $R^{14}$ is absent or H and the other is selected from the group consisting of H, —$C_{1-3}$ alkyl, —$C_{1-3}$ alkylene-halogen, and —$CF_3$; or $R^{13}$ and $R^{14}$ together form =O; and $R^{15}$ is absent or selected from the group consisting of H, —$C_{1-3}$ alkyl, —$C_{1-3}$ alkylene-halogen, and —$CF_3$; and (b) a compound of Formula II:

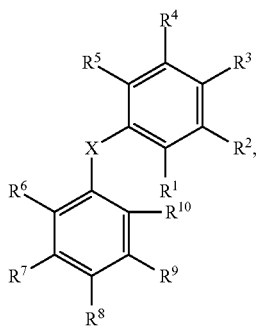

wherein:
one of $R^1$, $R^2$, $R^3$, $R^4$, and $R^5$ is halogen and the others are independently selected from the group consisting of H, —$C_{1-4}$ alkyl, —OH, and —O—$C_{1-3}$ alkyl;

$R^6$ and $R^{10}$ are independently selected from the group consisting of H, —$C_{1-3}$ alkyl, —OH, —O—$C_{1-3}$ alkyl, —SR, —$NR_2$, and halogen, wherein each R is independently H or —$C_{1-4}$ alkyl;

$R^7$ and $R^9$ are independently selected from the group consisting of H, —$C_{1-3}$ alkyl, —O—$C_{1-3}$ alkyl, —$NR_2$, and halogen, wherein each R is independently H or —$C_{1-4}$ alkyl;

$R^8$ is selected from the group consisting of H, —$C_{1-6}$ alkyl, —OH, —O—$C_{1-3}$ alkyl, —SR, —$CF_3$, —CN, —$NR_2$, —C(O)—OR, and halogen, wherein each R is independently H or —$C_{1-4}$ alkyl; and X is selected from the group consisting of —C($R^{11}R^{12}$)—, —N($R^{13}$)—, —O—, and —S—, wherein:
one of $R^{11}$ and $R^{12}$ is H and the other is selected from the group consisting of H, —$C_{1-3}$ alkyl, —$C_{1-3}$ alkylene-halogen, and —$CF_3$; or $R^{11}$ and $R^{12}$ together form =O; and $R^{13}$ is selected from the group consisting of H, —$C_{1-3}$ alkyl, —$C_{1-3}$ alkylene-halogen, and —$CF_3$.

A second aspect of the present technology relates to a method of inhibiting activity of a Ly6K protein in a cell, said method comprising: contacting the cell with an agent under conditions effective to inhibit activity of a Ly6K protein in the cell, wherein the agent is a compound (or pharmaceutically acceptable salt, ester, enol ether, enol ester, solvate, or hydrate thereof) according to the first aspect of the technology.

A third aspect of the present technology relates to a method of decreasing migration, colony formation, and/or proliferation of a cell, said method comprising: contacting the cell with an agent under conditions effective to decrease migration, colony formation, and/or proliferation of the cell, wherein the agent is a compound (or pharmaceutically acceptable salt, ester, enol ether, enol ester, solvate, or hydrate thereof) according to the first aspect of the technology.

A fourth aspect of the present technology relates to a method of modulating expression of a gene in a cell, said method comprising: contacting the cell with an agent under conditions effective to modulate expression of a gene in the cell, wherein the agent is a compound (or pharmaceutically acceptable salt, ester, enol ether, enol ester, solvate, or hydrate thereof) according to the first aspect of the technology and wherein the gene is selected from the group consisting of PD-L1, ABCC3, ABCG2, FGF-7, NANOG, PSCA, CD34, 2EB1, E-cadherin, and N-cadherin.

A fifth aspect of the present technology relates to a method of reducing suppression of the immune response to cancer in a subject, said method comprising: administering to the subject an agent under conditions effective to reduce suppression of the immune response to cancer in the subject, wherein the agent is a compound (or pharmaceutically acceptable salt, ester, enol ether, enol ester, solvate, or hydrate thereof) according to the first aspect of the technology.

A sixth aspect of the present technology relates to a method of decreasing tumorigenic growth of a cancer in a subject, said method comprising: administering an agent to the subject under conditions effective to decrease tumorigenic growth of a cancer in the subject, wherein the agent is a compound (or pharmaceutically acceptable salt, ester, enol ether, enol ester, solvate, or hydrate thereof) according to the first aspect of the technology.

A seventh aspect of the present technology relates to a method of treating or preventing in a subject a disorder mediated by Ly6K protein, said method comprising: administering an agent to the subject under conditions effective to treat or prevent the disorder, wherein the agent is a compound (or pharmaceutically acceptable salt, ester, enol ether, enol ester, solvate, or hydrate thereof) according to the first aspect of the technology.

We have identified the cell surface protein Ly6K as a potent activator of TGFβ signaling and tumor progression which is selectively expressed in cancer tissue. Ly6K levels are increased in 80% of TNBC and increased mRNA expression is associated with poor survival outcome in TNBC[8].

We have shown that Ly6K is required for in vivo tumor growth, and that it activates TGFβ signaling and epithelial to mesenchymal transition[9]. Ly6K is also required for IFNγ induced overexpression of PD-L1 in cancer cells[9]. Importantly, we found that knockdown or pharmacological inhibition of Ly6K inhibits PD-L1 expression in TNBC cells. More recently, we have identified two small molecule binders of Ly6K, NSC243928 and NSC11150, which inhibit multiple distinct aspects of the biological activity of Ly6K, like e.g. activation of TGFβ signaling, PD-L1 expression and tumor growth in syngeneic mice.

Based on these observations, we find that Ly6K plays an important role in tumor progression via activating the TGFβ and PD-L1 pathways and that targeting Ly6K by small molecule inhibitors will provide tissue-specific inhibition of TGFβ signaling and PD-L1 pathways in cancer cells. Our findings indicate that Ly6K leads to tumor progression and suppression of immune surveillance by enhancing TGFβ signaling, that Ly6K leads to tumor immune escape by upregulation of the checkpoint protein PD-L1, and that Ly6K can be targeted using small molecules to inhibit immune escape and tumor progression in TGFβ and PD-L1 pathways.

We show that Ly6K plays an important role in increased TGFβ and PD-L1 signaling using TNBC cell lines, clinical samples, syngeneic and xenograft tumor models. Its tissue-specific expression and its potent activation of tumor progression pathways makes it an attractive target for therapeutic intervention. For the first time, we present here two small molecule binders of Ly6K that efficiently inhibit TGFβ and PD-L1 pathways downstream of Ly6K. The present application provides compounds and methods for targeted immunotherapy for the treatment of TNBC by defining a novel therapeutic target for anti-TGFβ and inhibition of PD-L1 expression.

BRIEF DESCRIPTION OF THE DRAWINGS

The present technology can be better understood by reference to the following drawings. The drawings are merely exemplary to illustrate certain features that may be used singularly or in combination with other features and the present technology should not be limited to the embodiments shown.

DETAILED DESCRIPTION

Figure 1:
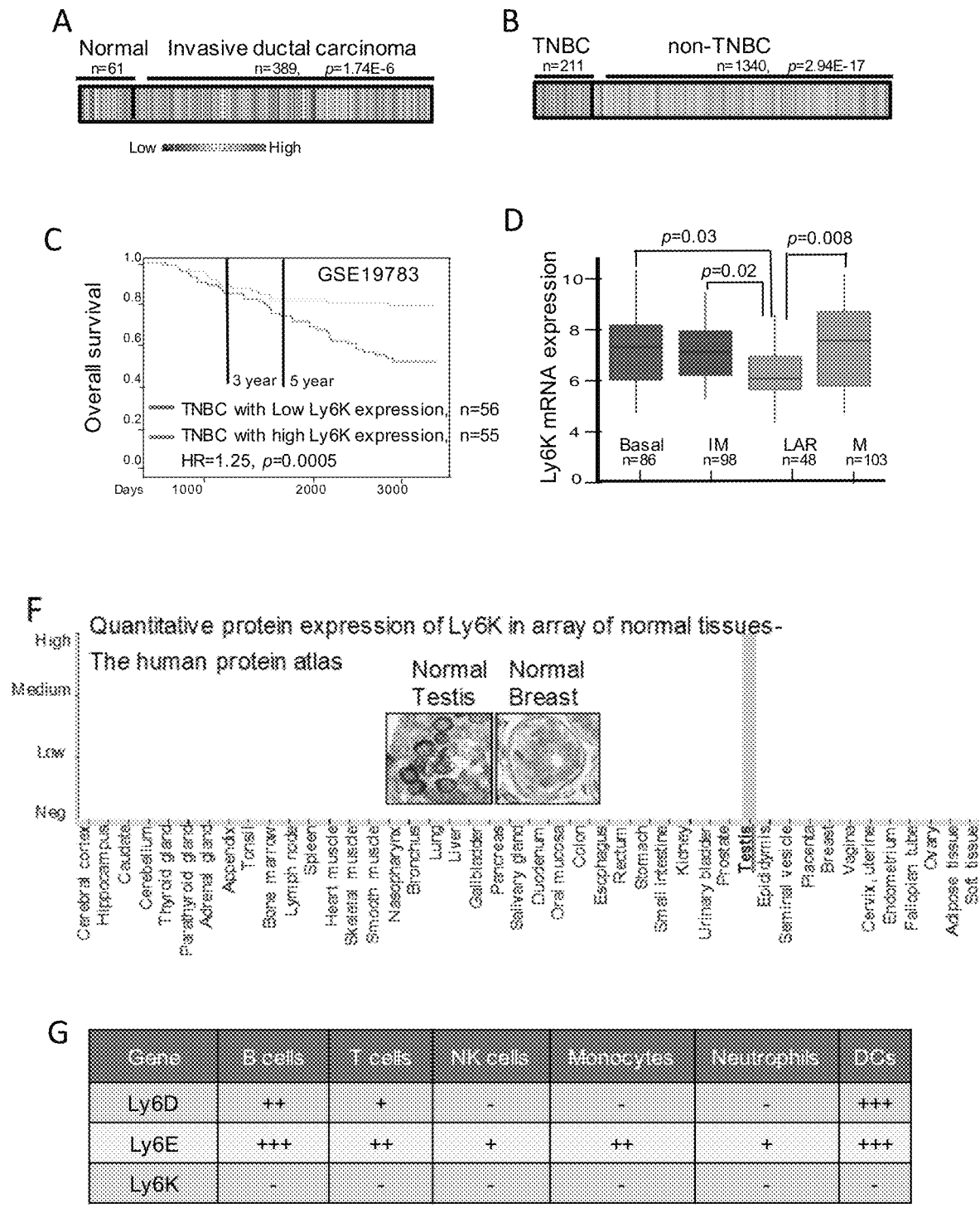
FIG. 1: Ly6K expression in TNBC. Oncomine data analysis was performed to visualize (A) increased mRNA expression of Ly6K in breast cancer compared to normal breast tissue using the cancer genome atlas data set, (B) increased mRNA expression in TNBC vs non-TNBC using the Curtis dataset10. Two sample T-test, p<0.05 significant. (C) Increased Ly6K expression is significantly associated with poor survival in TNBC (dataset ID: GSE19783) as visualized by the prognostic software tool ProGgene V2[11]. Using median gene expression value as bifurcating point, samples are divided into High and Low gene expression groups. Using survival data and continuous expression variable, survival analysis is done by fitting cox proportional hazards model using function "coxph" of library survival. Hazard ratio (HR) and log rank p value are retrieved from the fitted model. To create prognostic plot, High and Low expression categorical variable is used along with survival data. Plots are created using function 'survfit' of the same R library. HR, hazard ratio with p=0.0005, p<0.05 considered significant. Upper line: TNBC with low Ly6K expression; lower line: TNBC with high Ly6K expression. (D) Absolute Ly6K mRNA expression was quantified in TNBC subtypes described by Lehman et al[12]. Relevant GEO datasets (HGU133 Plus 2.0 arrays) of TNBC patients were normalized using Robust multi averaging RMA method and batch corrected using combat. The analysis was done in R, using packages oligo, sva and limma. n=number of tissue samples. Welch two sample T-test was applied to determine p values, p<0.05 considered significant. (F) The publicly available data at "The human protein atlas" shows quantification of IHC using a validated Ly6K antibody, rabbit polyclonal, affinity purified using the PrEST-antigen as affinity ligand HPA017770 (Sigma) in a panel of human normal tissues. The intensity of IHC labeling is shown on the Y-axis, X-axis shows name of organs tested. In the inset, IHC images are shown from normal testis and breast using Ly6K antibody. (G) The table is adopted from Lee et al, 2013[13], which shows mRNA expression of Ly6D and Ly6E genes in purified immune cells. Ly6K mRNA expression was not detected in immune cells.

The following detailed description is presented to enable any person skilled in the art to make and use the subject technology. For purposes of explanation, specific nomenclature is set forth to provide a thorough understanding of the present invention. However, it will be apparent to one skilled in the art that these specific details are not required to practice the technology. Descriptions of specific applications are provided only as representative examples. The present technology is not intended to be limited to the embodiments shown, but is to be accorded the widest possible scope consistent with the principles and features disclosed herein. Preferences and options for a given aspect, feature, or parameter of the invention should, unless the context indicates otherwise, be regarded as having been disclosed in combination with any and all preferences and options for all other aspects, features, and parameters of the invention.

This technology relates to compounds that inhibit Ly6K.

"Ly6K" refers to lymphocyte antigen 6 family member K proteins. Suitable Ly6K proteins include human Ly6K (e.g., GenBank Accession No. AAI17145.1, which is hereby incorporated by reference in its entirety) and non-human homologs of human Ly6K. Non-human homologs refer to proteins that are structurally and functionally similar to human Ly6K. Homologs have been identified, for example, in other primates (e.g., *Pan troglodytes* (chimpanzee), *Pongo abeli* (orangutan), *Macaca mulatta* (Rhesus monkey), Gorillas) and in rodents (e.g., mouse, rat).

Homologs of human Ly6K also include, for example, proteins that comprise an amino acid sequence that is at least about 80%, 85%, 90%, 91%, 92%, 93%, 94%, 95%, 96%, 97%, 98%, 99%, or 100% identical to that of human Ly6K. Percent identity as used herein refers to the comparison of one amino acid (or nucleic acid) sequence to another, as scored by matching amino acids (or nucleic acids). Percent identity is determined by comparing a statistically significant number of the amino acids (or nucleic acids) from two sequences and scoring a match when the same two amino acids (or nucleic acids) are present at a position. The percent identity can be calculated by any of a variety of alignment algorithms known and used by persons of ordinary skill in the art.

Compounds

The compounds of the present technology include Ly6K inhibitors (or pharmaceutically acceptable salts, esters, enol ethers, enol esters, solvates, or hydrates thereof) of Formula I and Formula II (see Table 1).

TABLE 1

Ly6K Inhibitors.

Formula I                                      Formula II

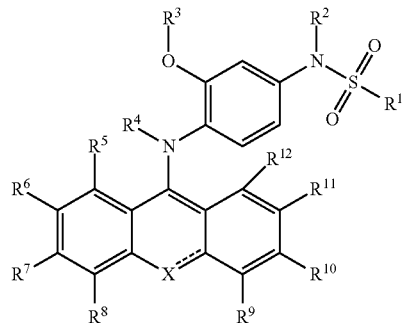                          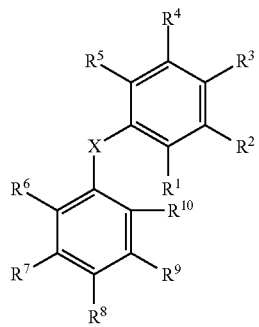

or salt thereof (e.g., alkylsulfonic acid salt,
e.g., methanesulfonic acid salt)

----- : a single or double bond $R^1$: —$C_{1-8}$ alkyl, —$C_{3-8}$ cycloalkyl, aryl, heterocyclyl, heteroaryl, -phenylene-$NH_2$, or —$C_{1-4}$ alkylene-$NH_2$
$R^2$: H, —$C_{1-3}$ alkyl, or —C(O)—$C_{1-5}$ alkyl
$R^3$: —$C_{1-6}$ alkyl or —$C_{1-3}$ alkylene-OH
$R^4$: H or —$C_{1-6}$ alkyl
$R^5$: H, —$C_{1-3}$ alkyl, —$NO_2$, —O—$C_{1-3}$ alkyl, halogen, —$NR_2$, or —C(O)—OR; each R is H or —$C_{1-4}$ alkyl
$R^6$: H, —$C_{1-4}$ alkyl, —$NR_2$, —$NO_2$, —O—$C_{1-3}$ alkyl, halogen, or —C(O)—OR; each R is H or —$C_{1-4}$ alkyl
$R^7$: H, —$C_{1-4}$ alkyl, —$C_{1-3}$ alkylene-SH, —CN, —$CF_3$, —$NR_2$, —$NO_2$, N=$N^+$=$N^-$, —NH—N=$N^+$—$C_{1-3}$ alkyl, —NH—C(O)—$C_{1-3}$ alkyl, —NH—C(O)—O—$C_{1-3}$ alkyl, —OR, —SR, —S—$C_{1-3}$ alkylene-SH, —$S(O_2)$—$C_{1-3}$ alkyl, —NH—$SO_2$—$C_{1-3}$ alkyl, or halogen; each R is H or —$C_{1-4}$ alkyl
$R^8$: H, —$C_{1-3}$ alkyl, —$C_{1-3}$ alkylene-C(O)—$NH_2$, —CN, —C—$NR_2$, —O—$C_{1-3}$ alkyl, halogen, or phenyl; each R is H or —$C_{1-4}$ alkyl
$R^9$: H, —$C_{1-3}$ alkyl, —$C_{1-3}$ alkylene-C(O)—$NH_2$, —CN, —C—$NR_2$, —O—$C_{1-3}$ alkyl, halogen, or phenyl; each R is H or —$C_{1-4}$ alkyl
$R^{10}$: H, —$C_{1-4}$ alkyl, —$C_{1-3}$ alkylene-SH, —CN, —$CF_3$, —$NR_2$, —$NO_2$, —N=$N^+$=$N^-$, —NH—N=$N^-$—$C_{1-3}$ alkyl, —NH—C(O)—$C_{1-3}$ alkyl, —NH—C(O)—O—$C_{1-3}$ alkyl, —OR, —SR, —S—$C_{1-3}$ alkylene-SH, —$S(O_2)$—$C_{1-3}$ alkyl, —NH—$SO_2$—$C_{1-3}$ alkyl, or halogen; each R is H or $C_{1-4}$ alkyl
$R^{11}$: H, —$C_{1-4}$ alkyl, —$NR_2$, —$NO_2$, —O—$C_{1-3}$ alkyl, halogen, or —C(O)—OR; each R is H or $C_{1-4}$ alkyl
$R^{12}$: H, —$C_{1-3}$ alkyl, —$NO_2$, —O—$C_{1-3}$ alkyl, halogen, —$NR_2$, or —C(O)—OR; each R is H or $C_{1-4}$ alkyl
X: —C($R^{13}$, $R^{14}$)—, —N($R^{15}$)—, —O—, or —S—
$R^{13}$, $R^{14}$: one is absent or H and the other is H, —$C_{1-3}$ alkyl, —$C_{1-3}$ alkylene-halogen, or —$CF_3$; or $R^{13}$ and $R^{14}$ together form =O;
$R^{15}$: absent, H, —$C_{1-3}$ alkyl, —$C_{1-3}$ alkylene-halogen, or —$CF_3$
An embodiment of Formula I ----- : a single or double bond $R^1$: —$C_{1-8}$ alkyl, —$C_{3-8}$ cycloalkyl, aryl, heterocyclyl, or heteroaryl
$R^2$: H or —$C_{1-3}$ alkyl
$R^3$: —$C_{1-6}$ alkyl or —$C_{1-3}$ alkylene-OH
$R^4$: H or —$C_{1-6}$ alkyl
$R^5$: H, —$C_{1-3}$ alkyl, —$NO_2$, —O—$C_{1-3}$ alkyl, halogen, —$NR_2$, or —C(O)—OR; each R is H or —$C_{1-4}$ alkyl
$R^6$: H, —$C_{1-4}$ alkyl, —$NR_2$, —$NO_2$, —O—$C_{1-3}$ alkyl, halogen, or —C(O)—OR; each R is H or —$C_{1-4}$ alkyl
$R^7$: H, —$C_{1-4}$ alkyl, —$C_{1-3}$ alkylene-SH, —CN, —$CF_3$, —$NR_2$, —$NO_2$, —OR, —SR, or halogen; each R is H or —$C_{1-4}$ alkyl
$R^8$: H, —$C_{1-3}$ alkyl, —CN, —O—$C_{1-3}$ alkyl, halogen, or phenyl; each R is H or —$C_{1-4}$ alkyl
$R^9$: H, —$C_{1-3}$ alkyl, —CN, —O—$C_{1-3}$ alkyl, halogen, or phenyl; each R is H or —$C_{1-4}$ alkyl
$R^{10}$: H, —$C_{1-4}$ alkyl, —$C_{1-3}$ alkylene-SH, —CN, —$CF_3$, —$NR_2$, —$NO_2$, —OR, —SR, or halogen; each is H or $C_{1-4}$ alkyl
$R^{11}$: H, —$C_{1-4}$ alkyl, —$NR_2$, —$NO_2$, —O—$C_{1-3}$ alkyl, halogen, or $R^1$, $R^2$, $R^3$, $R^4$, $R^5$: one is halogen and the others are H, —$C_{1-4}$ alkyl, —OH, or —O—$C_{1-3}$ alkyl
$R^6$, $R^{10}$: —$C_{1-3}$ alkyl, —OH, —O—$C_{1-3}$ alkyl, —SR, —$NR_2$, or halogen; each R is H or —$C_{1-4}$ alkyl
$R^7$, $R^9$: H, —$C_{1-3}$ alkyl, —O—$C_{1-3}$ alkyl, —$NR_2$, or halogen; each R is H or —$C_{1-4}$ alkyl
$R^8$: H, —$C_{1-6}$ alkyl, —OH, —O—$C_{1-3}$ alkyl, —SR, —$CF_3$, —CN, —$NR_2$, —C(O)—OR, or halogen; each R is H or —$C_{1-4}$ alkyl
X: —C($R^{11}R^{12}$)—, —N($R^{13}$)—, —O—, or —S—
$R^{11}$, $R^{12}$: one is H and the other is H, —$C_{1-3}$ alkyl, —$C_{1-3}$ alkylene-halogen, or —$CF_3$; or $R^{11}$ and $R^{12}$ together form =O
$R^{13}$: H, —$C_{1-3}$ alkyl, —$C_{1-3}$ alkylene-halogen, or —$CF_3$ An embodiment of Formula II $R^1$, $R^2$, $R^3$: one is halogen and the others are H, —$C_{1-4}$ alkyl, —OH, or —O—$C_{1-3}$ alkyl
$R^4$, $R^5$: H or —$C_{1-4}$ alkyl
$R^6$: —OR; R is H or —$C_{1-3}$ alkyl
$R^7$, $R^9$, $R^{10}$: H or —$C_{1-3}$ alkyl
$R^8$: —OH or —$C_{1-3}$ alkyl
X: —C($R^{11}R^{12}$)—, —N($R^{13}$)—, —O—, or —S—
$R^{11}$, $R^{12}$: one is H and the other is H, —$C_{1-3}$ alkyl, —$C_{1-3}$ alkylene-halogen, or —$CF_3$; or $R^{11}$ and $R^{12}$ together form =O
$R^{13}$: H, —$C_{1-3}$ alkyl, —$C_{1-3}$ alkylene-halogen, or —$CF_3$ TABLE 1-continued Ly6K Inhibitors.

| Formula I | Formula II |
|---|---|
| —C(O)—OR; each R is H or $C_{1-4}$ alkyl<br>$R^{12}$: H, —$C_{1-3}$ alkyl, —$NO_2$, —O—$C_{1-3}$ alkyl, halogen, —$NR_2$, or<br>—C(O)—OR; each R is H or $C_{1-4}$ alkyl<br>X: —C($R^{13}$, $R^{14}$)—, —N($R^{15}$)—, —O—, —S—<br>$R^{13}$, $R^{14}$: one is absent or H and the other is H, —$C_{1-3}$ alkyl,<br>—$C_{1-3}$ alkylene-halogen, or —$CF_3$: or $R^{13}$ and $R^{14}$<br>together form =O;<br>$R^{15}$: absent, H, —$C_{1-3}$ alkyl, —$C_{1-3}$ alkylene-halogen, or —$CF_3$<br>An embodiment of Formula I | An embodiment of Formula II |
| - - - - - : a single or double bond | $R^1$, $R^2$: H, —$C_{1-4}$ alkyl, —OH, or —O—$C_{1-3}$ alkyl |
| $R^1$: —$C_{1-8}$ alkyl, —$C_{3-8}$ cycloalkyl, aryl, heterocyclyl, or heteroaryl<br>$R^2$, $R^4$, $R^5$, $R^9$, $R^{10}$, $R^{11}$, $R^{12}$: H or —$C_{1-3}$ alkyl (e.g., H)<br>$R^3$: —$C_{1-6}$ alkyl or —$C_{1-3}$ alkylene-OH<br>$R^6$: H, —$C_{1-4}$ alkyl, —$NR_2$, —$NO_2$, —O—$C_{1-3}$ alkyl, halogen, or<br>—C(O)—OR; each R is H or —$C_{1-4}$ alkyl<br>$R^7$: H, —$C_{1-4}$ alkyl, —$C_{1-3}$ alkylene-SH, —CN, —$CF_3$, —$NR_2$, —$NO_2$,<br>—OR, —SR, or halogen; each R is H or —$C_{1-4}$ alkyl<br>$R^8$: H, —$C_{1-3}$ alkyl, —CN, —O—$C_{1-3}$ alkyl, halogen, or phenyl; each R<br>is H or —$C_{1-4}$ alkyl<br>X: —C($R^{13}$, $R^{14}$)—, —N($R^{15}$)—, —O—, or —S—<br>$R^{13}$, $R^{14}$: one is absent or H and the other is H, —$C_{1-3}$ alkyl,<br>—$C_{1-3}$ alkylene-halogen, or —$CF_3$: or $R^{13}$ and $R^{14}$<br>together form =O;<br>$R^{15}$: absent, H, —$C_{1-3}$ alkyl, —$C_{1-3}$ alkylene-halogen, or —$CF_3$<br>An embodiment of Formula I | $R^3$: halogen<br>$R^4$, $R^5$: H or —$C_{1-4}$ alkyl<br>$R^6$: —OR; R is H or —$C_{1-3}$ alkyl<br>$R^7$, $R^9$, $R^{10}$: H or —$C_{1-3}$ alkyl<br>$R^8$: —OH or —O—$C_{1-3}$ alkyl<br>X: —C($R^{11}R^{12}$)—, —N($R^{13}$)—, —O—, or —S—<br>$R^{11}$, $R^{12}$: one is H and the other is H, —$C_{1-3}$ alkyl, —$C_{1-3}$<br>alkylene-halogen, or —$CF_3$; or $R^{11}$ and $R^{12}$ together<br>form =O<br>$R^{13}$: H, —$C_{1-3}$ alkyl, —$C_{1-3}$ alkylene-halogen, or —$CF_3$<br><br>An embodiment of Formula II |
| - - - - - : a double bond | $R^1$, $R^2$: H or —$C_{1-4}$ alkyl (e.g., H) |
| $R^1$: —$C_{1-8}$ alkyl (e.g., —$C_{1-4}$ alkyl, e.g., ethyl))<br>$R^2$, $R^4$, $R^5$, $R^8$, $R^9$, $R^{10}$, $R^{11}$, $R^{12}$: H or alkyl (e.g., H)<br>$R^3$: —$C_{1-6}$ alkyl (e.g., —$C_{1-3}$ alkyl, e.g., methyl)<br>$R^6$, $R^7$: H or —$C_{1-4}$ alkyl (e.g., H)<br>X: —N($R^{15}$)—, $R^{15}$ is absent<br><br><br>An embodiment of Formula I | $R^3$: halogen (e.g., Cl)<br>$R^4$, $R^5$, $R^7$, $R^9$, $R^{10}$: H<br>$R^6$: —O—$C_{1-3}$ alkyl (e.g., —O—$CH_3$)<br>$R^8$: —OH<br>X: —C($R^{11}R^{12}$)—<br>$R^{11}$, $R^{12}$: one is H and the other is H, —$C_{1-3}$ alkyl, —$C_{1-3}$<br>alkylene-halogen, or —$CF_3$; or $R^{11}$ and $R^{12}$ together<br>form =O<br>An embodiment of Formula II |
| - - - - - : a double bond | $R^1$, $R^2$: H or —$C_{1-4}$ alkyl (e.g., H) |
| $R^1$: —$C_{1-8}$ alkyl (e.g., —$C_{1-4}$ alkyl, e.g., ethyl))<br>$R^2$, $R^4$, $R^5$, $R^9$, $R^{10}$, $R^{11}$, $R^{12}$: H<br>$R^3$: —$C_{1-6}$ alkyl (e.g., —$C_{1-3}$ alkyl, e.g., methyl)<br>$R^6$, $R^7$: H or —$C_{1-4}$ alkyl (e.g., H)<br>$R^8$: H or —$C_{1-3}$ alkyl (e.g., H)<br>X: —N($R^{15}$)—, $R^{15}$ is absent | $R^3$: halogen (e.g., Cl)<br>$R^4$, $R^5$, $R^7$, $R^9$, $R^{10}$: H<br>$R^6$: —OH<br>$R^8$: —OH<br>X: —C($R^{11}R^{12}$)—<br>$R^{11}$, $R^{12}$: one is H and the other is H, —$C_{1-3}$ alkyl, —$C_{1-3}$<br>alkylene-halogen, or —$CF_3$; or $R^{11}$ and $R^{12}$ together<br>form =O |

Figure 15:
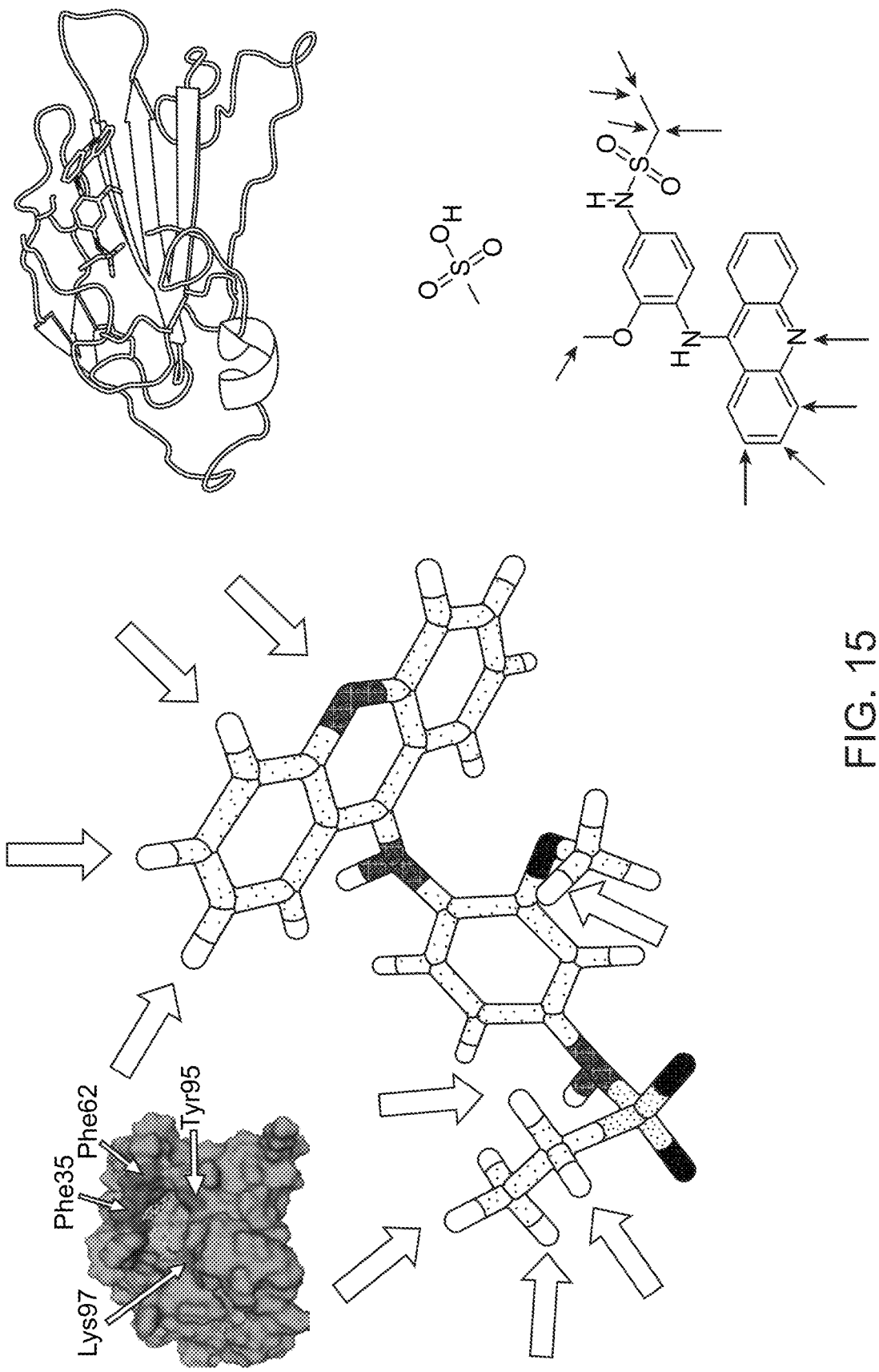
FIG. 15. Schematic model of binding interaction between Ly6K and small molecule NSC243928 (4'-(9-Acridinylamino)-3'-methoxyethanesulfonanilide methanesulfonate).
Figure 16:
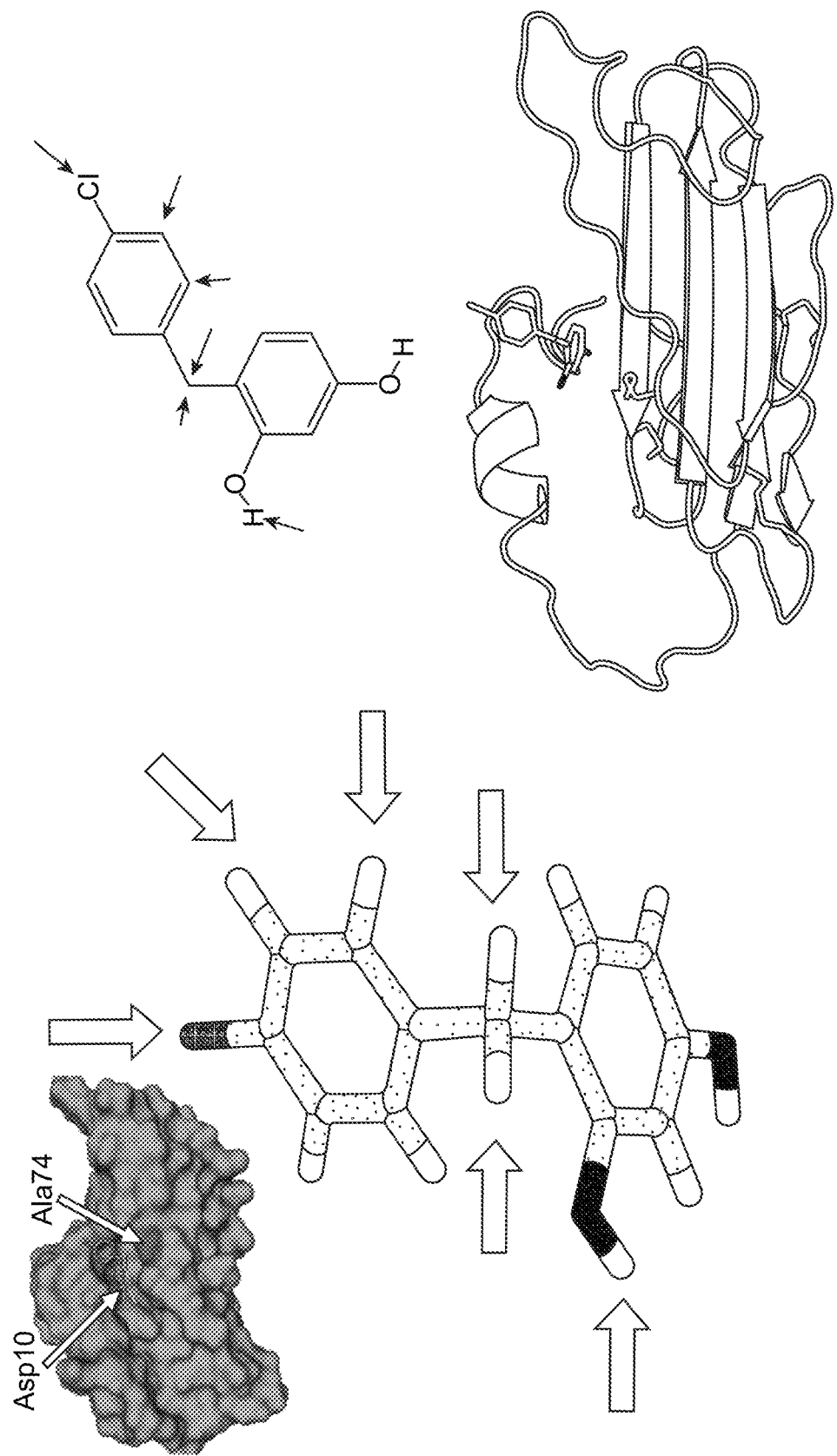
FIG. 16. Schematic model of binding interaction between Ly6K and small molecule NSC11150 (4-(4-chlorobenzyl) benzene-1,3-diol).

Formula I compounds include NSC243928 and analogs thereof. Formula II compounds include NSC11150 and analogs thereof. FIGS. 15 and 16 show the rationale for making analogs of NSC243928 (FIG. 15) and NSC11150 (FIG. 16) within Formulae I and II, respectively, based on the interaction between these compounds and their binding sites on Ly6K. The arrows indicate the atoms that do not appear to be involved in the binding interaction; it is expected that the compounds can tolerate considerable variation at these positions while maintaining their activity.

The term "alkyl" means an aliphatic saturated or unsaturated hydrocarbon group, which may be straight or branched, having about 1 to about 8 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl. The term "alkylene" means a divalent counterpart of an alkyl as defined herein.

The term "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane.

The term "aryl" refers to aromatic monocyclic or polycyclic ring system containing from 6 to 19 carbon atoms, where the ring system may be optionally substituted. Exemplary aryl groups include, but are not limited to, groups such as phenyl, naphthyl, azulenyl, phenanthrenyl, anthracenyl, fluorenyl, pyrenyl, triphenylenyl, chrysenyl, and naphthacenyl. In at least one embodiment, the aryl is a monocyclic ring system containing from 6 to 9 carbon atoms.

The term "heterocyclyl" refers to a stable 3- to 18-membered ring radical which consists of carbon atoms and from one to five heteroatoms selected from the group consisting of nitrogen, oxygen and sulfur. For purposes of this technology, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. In at least one embodiment, the heterocyclyl is a monocyclic ring radical containing from 3 to 9 carbon atoms.

The term "heteroaryl" refers to an aromatic ring radical which consists of carbon atoms and from one to five heteroatoms selected from the group consisting of nitrogen, oxygen, and sulfur. For purposes of this invention the heteroaryl may be a monocyclic or polycyclic ring system; and the nitrogen, carbon, and sulfur atoms in the heteroaryl ring may be optionally oxidized; the nitrogen may optionally be quaternized. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. In at least one embodiment, the heteroaryl is a monocyclic or polycyclic ring system containing from 6 to 19 ring atoms. In at least one embodiment, the heteroaryl is a monocyclic ring system containing from 6 to 9 ring atoms.

Further heterocycles and heteroaryls are described in COMPREHENSIVE HETEROCYCLIC CHEMISTRY: THE STRUCTURE, REACTIONS, SYNTHESIS AND USE OF HETEROCYCLIC COMPOUNDS Vol. 1-8 (Alan R. Katritzky et al. eds., 1$^{st}$ ed. 1984), which is hereby incorporated by reference in its entirety.

The term "halo" or "halogen" means fluoro, chloro, bromo, or iodo.

The compounds of the present technology (or pharmaceutically acceptable salts, esters, enol ethers, enol esters, solvates, or hydrates thereof) can optionally be modified to include a tag. A "tag" as used herein includes any labeling moiety that facilitates the detection, quantitation, isolation, and/or purification of a compound (i.e., a compound of the present technology, a compound-glutaminase GLS1 protein conjugate as described infra, a conjugated compound/inhibitor as described infra, and/or a conjugated glutaminase GLS1 protein as described infra). Methods for modifying small molecules to include tags are well known in the art.

For example, click chemistry (see, e.g., U.S. Pat. No. 7,375,234 to Sharpless et al., which is hereby incorporated by reference in its entirety) may be used to attach a tag to a compound.

Suitable tags include purification tags, labels including radioactive or fluorescent labels, enzymatic tags, prosthetic groups, luminescent materials, bioluminescent materials, positron emitting metals, nonradioactive paramagnetic metal ions, and any other signal suitable for detection and/or measurement by radiometric, colorimetric, fluorometric, size-separation, or precipitation means, or other means known in the art.

Purification tags, such as, but not limited to, maltose-binding protein (MBP-), poly-histidine ($His_6$-), or a gluta-thione-S-transferase (GST-), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{123}I$, $^{131}I$, $^{111}In$, $^{112}In$, $^{113}In$, $^{115}In$, $^{99}TC$, $^{213}Bi$, $^{14}C$, $^{51}Cr$, $^{153}Gd$, $^{159}Gd$, $^{68}Ga$, $^{67}Ga$, $^{68}Ge$, $^{166}Ho$, $^{140}La$, $^{177}Lu$, $^{54}Mn$, $^{99}Mo$, $^{103}Pd$, $^{32}P$, $^{142}Pr$, $^{149}Pm$, $^{186}Re$, $^{188}Re$, $^{105}Rh$, $^{97}Ru$, $^{153}Sm$, $^{47}Sc$, $^{75}Se$, $^{85}Sr$, $^{35}S$, $^{201}Ti$, $^{113}Sn$, $^{113}Sn$, $^{3}H$, $^{133}Xe$, $^{169}Yb$, $^{175}Yb$, $^{90}Y$, and $^{65}Zn$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Further examples include positron emitting metals using various positron emission tomographies, and nonradioactive paramagnetic metal ions.

Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, Texas Red, and umbelliferone. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, 0-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., Methods for the Preparation of Enzyme-Antibody Conjugates for Use in Enzyme Immunoassay, in METHODS IN ENZYMOLOGY 147-66 (Langone et al. eds., 1981), which is hereby incorporated by reference in its entirety.

Prosthetic group complexes include, but are not limited to, streptavidin/biotin and avidin/biotin. Alternatively, the compound can be conjugated to a luminescent or bioluminescent material including, but not limited to, luminol, luciferase, luciferin, and aequorin.

The compounds of the present technology (or pharmaceutically acceptable salts, esters, enol ethers, enol esters, solvates, or hydrates thereof) can optionally be modified to include an attachment to a solid surface, such as a fibrous test strip, a column, a multi-well microliter plate, a test tube, or beads. Methods for attaching small molecules to such surfaces, including covalent attachment (for example via click chemistry, as described supra) as well as non-covalent attachment through the use of antibody-antigen partners, complementary nucleic acids, etc., are well known in the art.

Pharmaceutically acceptable salts include, but are not limited to, amine salts, such as but not limited to, N, N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methyl-benzimidazole, diethylamine and other alkylamines, piperazine, and tris (hydroxymethyl) aminomethane; alkali metal salts, such as but not limited to, lithium, potassium, and sodium; alkali earth metal salts, such as but not limited to, barium, calcium, and magnesium; transition metal salts, such as but not limited to, zinc; and other metal salts, such as but not limited to, sodium hydrogen phosphate and disodium phosphate; and also including, but not limited to, salts of mineral acids, such as but not limited to, hydrochlorides and sulfates; and salts of organic acids, such as but not limited to, acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutically acceptable enol ethers include, but are not limited to, derivatives of formula C=C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C (OC (O) R) where R is hydrogen, alkyl, alkenyl, alkynyl, aryl, heteroaryl, cycloalkyl, or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

The Ly6K inhibitor compound may be administered in the form of a pharmaceutical composition comprising the compound (or a pharmaceutically acceptable salt, ester, enol ether, enol ester, solvate, or hydrate thereof). The pharmaceutical compositions can comprise a compound of the present technology and a pharmaceutically acceptable carrier and, optionally, one or more additional active agent(s) as discussed below.

Numerous standard references are available that describe procedures for preparing various formulations suitable for administering the compounds according to the invention. Examples of potential formulations and preparations are contained, for example, in the HANDBOOK OF PHARMACEUTICAL EXCIPIENTS (American Pharmaceutical Association, current edition), PHARMACEUTICAL DOSAGE FORMS: TABLETS (Lieberman et al. eds., Marcel Dekker, Inc., pubs., current edition), and REMINGTON'S PHARMACEUTICAL SCIENCES 1553-93 (Arthur Osol ed., current edition), which are hereby incorporated by reference in their entirety.

Any pharmaceutically acceptable liquid carrier suitable for preparing solutions, suspensions, emulsions, syrups and elixirs may be employed in the pharmaceutical composition. Compounds may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, excipients, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

It will be understood that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

Methods

The term "inhibit" or "inhibiting" as it applies to inhibiting activity of a Ly6K protein, inhibiting TGF-β1, SMAD2/3, IFNγ or Stat1 signaling, inhibiting SMAD2/3 or Stat1 phosphorylation, or inhibiting PD-L1 expression, means to suppress, decrease, diminish, or lower activity/signaling/phosphorylation/expression. In all cases, inhibition can be partial or complete.

The term "modulating" as it refers to expression of a gene means to increase or decrease expression and includes modulating transcription, translation, and/or post-translational processing. In at least one embodiment, modulating expression means increasing or decreasing the amount of mRNA produced. In at least one embodiment, modulating expression means increasing or decreasing the amount of mature protein produced.

The term "treatment" or "treating" means any manner in which one or more of the symptoms of a disease or disorder are ameliorated or otherwise beneficially altered. Treatment also encompasses any pharmaceutical use of the compositions herein, such as use for treating diseases or disorders mediated by Ly6K. Disorders mediated by Ly6K include disorders in which Ly6K is overexpressed and/or overactive. Suitable disorders include, without limitation, cancer.

Ly6K expression has been shown to be significantly increased in at least breast cancer, bladder cancer, brain cancer, cancer of the central nervous system, kidney cancer, lung cancer, ovarian cancer, gastric cancer, colorectal cancer, cervical cancer, head and neck cancer, esophageal cancer, and pancreatic cancer as compared to their normal counterparts. (E.g., Luo et al., *Oncotarget* 7(10):11165-93 (2016); Al Hossiny et al., *Cancer Res.* 76(11):3376-86 (2016), each of which is hereby incorporated by reference in its entirety.) High Ly6K expression has also been shown to be significantly correlated with poor clinical outcome in at least breast cancer, bladder cancer, brain cancer, cancer of the central nervous system, kidney cancer, lung cancer, ovarian cancer, gastric cancer, colorectal cancer, cervical cancer, head and neck cancer, esophageal cancer, and pancreatic cancer. (E.g., Luo et al., *Oncotarget* 7(10):11165-93

(2016); Al Hossiny et al., *Cancer Res.* 76(11):3376-86 (2016), each of which is hereby incorporated by reference in its entirety.) Ly6K is also more highly expressed in triple negative breast cancer, with the mesenchymal, basal, and immunomodulatory subtypes showing the highest expression (see, e.g., Examples infra).

In all aspects of the present technology directed to methods involving contacting a cell with one or more compounds, contacting can be carried out using methods that will be apparent to the skilled artisan, and can be done in vitro, ex vivo, or in vivo.

Compounds of the present invention may be delivered directly to a targeted cell/tissue/organ. Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell, including its transport across the blood-brain barrier; and/or to facilitate its uptake by a target cell (e.g., its transport across cell membranes).

In vivo administration can be accomplished either via systemic administration to the subject or via targeted administration to affected tissues, organs, and/or cells, as described above. Typically, the therapeutic agent (i.e., a Ly6K inhibitor compound) will be administered to a patient in a vehicle that delivers the therapeutic agent(s) to the target cell, tissue, or organ. Typically, the therapeutic agent will be administered as a pharmaceutical formulation, such as those described above.

The compounds can be administered, e.g., by intravenous injection, intramuscular injection, subcutaneous injection, intraperitoneal injection, topical application, sublingual, intraarticular (in the joints), intradermal, buccal, ophthalmic (including intraocular), intranasally (including using a cannula), or by other routes. The compounds can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g., WO 97/11682, which is hereby incorporated by reference in its entirety) via a liposomal formulation (see, e.g., European Patent No. 736299, WO 99/59550, and WO 97/13500, which are hereby incorporated by reference in their entirety), via formulations described in WO 03/094886, which is hereby incorporated by reference in its entirety, or in some other form. The compounds can also be administered transdermally (i.e., via reservoir-type or matrix-type patches, microneedles, thermal poration, hypodermic needles, iontophoresis, electroporation, ultrasound or other forms of sonophoresis, jet injection, or a combination of any of the preceding methods (e.g., Prausnitz et al., *Nature Reviews Drug Discovery* 3:115 (2004), which is hereby incorporated by reference in its entirety). The compounds can be administered locally, for example, at the site of injury to an injured blood vessel. The compounds can be coated on a stent. The compounds can be administered using high-velocity transdermal particle injection techniques using the hydrogel particle formulation described in U.S. Patent Publication No. 20020061336, which is hereby incorporated by reference in its entirety. Additional particle formulations are described in WO 00/45792, WO 00/53160, and WO 02/19989, which are hereby incorporated by reference in their entirety. An example of a transdermal formulation containing plaster and the absorption promoter dimethylisosorbide can be found in WO 89/04179, which is hereby incorporated by reference in its entirety. WO 96/11705, which is hereby incorporated by reference in its entirety, provides formulations suitable for transdermal administration.

For use as aerosols, a compound in solution or suspension may be packaged in a pressurized aerosol container together with suitable propellants, for example, hydrocarbon propellants like propane, butane, or isobutane with conventional adjuvants. The compounds also may be administered in a non-pressurized form.

Exemplary delivery devices include, without limitation, nebulizers, atomizers, liposomes (including both active and passive drug delivery techniques) (Wang & Huang, *Proc. Nat'l Acad. Sci. USA* 84:7851-55 (1987); Bangham et al., *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; U.S. Pat. No. 5,059,421 to Loughrey et al.; Wolff et al., *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the compound to the desired organ, tissue, or cells in vivo.

Contacting (including in vivo administration) can be carried out as frequently as required and for a duration that is suitable to provide the desired effect. For example, contacting can be carried out once or multiple times, and in vivo administration can be carried out with a single sustained-release dosage formulation or with multiple (e.g., daily) doses.

The amount to be administered will, of course, vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the compound are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

The compounds can be administered alone or as an active ingredient of a pharmaceutical formulation, such as those described above. The compounds of the present invention can be administered in a form where the active ingredient is substantially pure.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, primates (e.g., humans, chimpanzees, gorillas, orangutans, Rhesus monkeys), domestic animals, such as feline (e.g., cats) or canine (e.g., dogs) subjects, farm animals, such as but not limited to bovine (e.g., cows), equine (e.g., horses), caprine (e.g., goats), ovine (e.g., sheep), and porcine (e.g., pigs) subjects, wild or non-domestic animals (whether in the wild or in a zoological garden), research animals, such as mice, rats, rabbits, guinea pigs, goats, sheep, pigs, dogs, cats, horses, cows, camels, llamas, monkeys, zebrafish, etc., avian species, such as chickens, turkeys, songbirds, etc., i.e., for veterinary medical use.

The current literature indicates that Ly6K is not required for normal cell function except for spermatogenesis. Thus, in some embodiments the subject is selected from a population in which causing a deleterious effect on male fertility as a result of administering a Ly6K inhibitor would not be a concern, for example in females or in vasectomized and/or sterile males.

These aspects of the present technology are further illustrated by the following examples. All references cited throughout this application, including in the drawings and Examples, are hereby incorporated by reference in their entirety.

EXAMPLES

The following examples are provided to illustrate embodiments of the present technology, but they are by no means intended to limit its scope.

Example 1—Role of Ly6K in TGFβ and Immune Escape Pathways of Triple Negative Breast Cancer The present application provides a Ly6K-targeted strategy to inhibit TGFβ signaling and PD-L1 protein expression for the treatment of triple negative breast cancer (TNBC). Targeted therapies such as hormone therapy or anti-Her2 therapies are not effective for TNBC[1]. Although immunotherapy has led to a paradigm shift in cancer therapeutics, its effect in TNBC has been modest, at best[2]. TNBC affects younger women and has the worst overall survival rate among breast cancer subtypes[3]. The present application fulfills an urgent need to identify and develop novel, effective and safe approaches to treat TNBC.

Recent discoveries in triple negative breast cancer suggest that the immune checkpoint protein PD-L1 is increased in TNBC and that its increased expression contributes to tumor immune escape[4,5]. TGFβ signaling represents another key hub in cancer that activates both immune and non-immune associated pathways of tumor progression[6,7]. The widespread expression and essential function of TGFβ signaling and PD-L1 in many normal tissues, however, make them problematic targets for therapeutic intervention. Our laboratory has identified the cell surface protein Ly6K as a potent activator of TGFβ signaling and tumor progression which is selectively expressed in cancer tissue. Ly6K levels are increased in 80% of TNBC and increased mRNA expression is associated with poor survival outcome in TNBC[8]. We have shown that Ly6K is required for in vivo tumor growth, and that it activates TGFβ signaling and epithelial to mesenchymal transition[9]. Ly6K is also required for IFNγ induced overexpression of PD-L1 in cancer cells[9]. Importantly, we found that knockdown or pharmacological inhibition of Ly6K inhibits PD-L1 expression in TNBC cells and have identified two small molecule binders of Ly6K, NSC243928 and NSC11150, which inhibit multiple distinct aspects of the biological activity of Ly6K, e.g., activation of TGFβ signaling, PD-L1 expression and tumor growth in syngeneic mice.

Based on these observations, we note that Ly6K plays an important role in tumor progression via activating the TGFβ and PD-L1 pathways and have surprisingly found that targeting Ly6K by small molecule inhibitors provides tissue-specific inhibition of TGF signaling and PD-L1 pathways in cancer cells (Scheme 1).

Scheme 1: Role of Ly6K targeting for the treatment of TNBC.

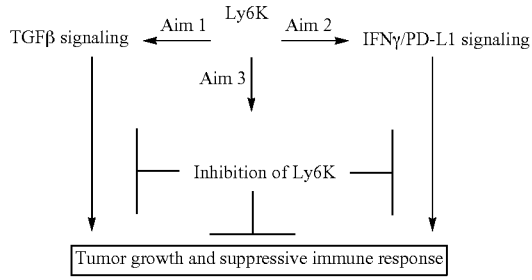

Without wishing to be bound by theory, we suggest that Ly6K leads to tumor progression and suppression of immune surveillance by enhancing TGFβ signaling, that Ly6K leads to tumor immune escape by upregulation of the checkpoint protein PD-L1, and that Ly6K can be targeted using small molecules to inhibit immune escape and tumor progression in TGFβ and PD-L1 pathways.

The observation that Ly6K plays an important role in increased TGFβ and PD-L1 signaling has been demonstrated using TNBC cell lines, clinical samples, syngeneic and xenograft tumor models. Its tissue-specific expression and its potent activation of tumor progression pathways makes it an attractive target for therapeutic intervention. For the first time, we present here two small molecule binders of Ly6K that efficiently inhibit TGFβ and PD-L1 pathways downstream of Ly6K. The present application provides for targeted immunotherapy for the treatment of TNBC by defining a novel therapeutic target for anti-TGFβ and inhibition of PD-L1 expression.

Ly6K is a Marker of Poor Outcome and a Valid Therapeutic Target in Triple Negative Breast Cancer (TNBC).

TNBC is a highly heterogeneous disease and composed of multiple subtypes[1]. TNBC patients suffer the worst outcome and have fewer therapeutic options compared to patients with estrogen receptor (ER) positive and human epidermal growth factor receptor 2 (Her 2) positive breast cancer[3]. Therefore, there is an urgent need to develop novel targeted treatments for this disease. We reported that 80% of TNBC cases have increased protein expression of Ly6K[9]. In agreement with the protein expression pattern, mRNA expression of Ly6K was also increased in TNBC compared to non-TNBC (FIG. 1A, B). We published a bioinformatics analysis of 130 clinical studies demonstrating that increased mRNA expression of Ly6K is associated with poor outcome in breast cancer and other solid malignancies[8].

New analysis shows that increased Ly6K mRNA expression is also linked to poor outcome in TNBC (basal subtype, data not available for other subtypes) (FIG. 1C). To test if Ly6K mRNA expression is associated with a distinct subtype of TNBC, we used a large gene expression dataset of various TNBC subtypes[10]. We performed meta-analysis to determine the absolute mRNA expression level of Ly6K on a scale of 0 (undetectable) to 12 (highest intensity) as defined by normalized signal intensity using inbuilt array controls. Ly6K mRNA levels were found to be higher in basal like (BL), immunomodulatory (IM), mesenchymal (M) than in luminal androgen receptor (LAR) TNBC. Further analysis is focused on the TNBC subtypes that express the highest levels of Ly6K, namely BL, IM and M using relevant cell line models (FIG. 1D). Among a panel of normal tissues, protein expression of Ly6K was found to be limited to testis (The Human Protein Atlas)[11,12] FIG. 1F). The absence of Ly6K protein expression in normal tissues was an important criterion to choose this gene for further study as opposed to Ly6E and Ly6D, which are also increased in TNBC[8]. Ly6E and Ly6D have high mRNA and protein expression in normal liver and bone marrow, and play an important role in hematopoiesis[13] (FIG. 1G). The normal function of Ly6K in testis is associated with spermatogenesis[14]. The current literature suggests that Ly6K is not required for normal cell function except for spermatogenesis. Therefore, it is plausible that future therapeutic approaches focused on targeting Ly6K should have minimal toxicity in female TNBC patients. Increased expression of Ly6K has been well documented in bladder, gastric, head and neck and ovarian cancer, so the therapeutic strategies aimed at Ly6K may be applied to multiple cancer types[8,15-17].

Ly6K Is Required for Increased TGFβ Signaling.

Figure 2:
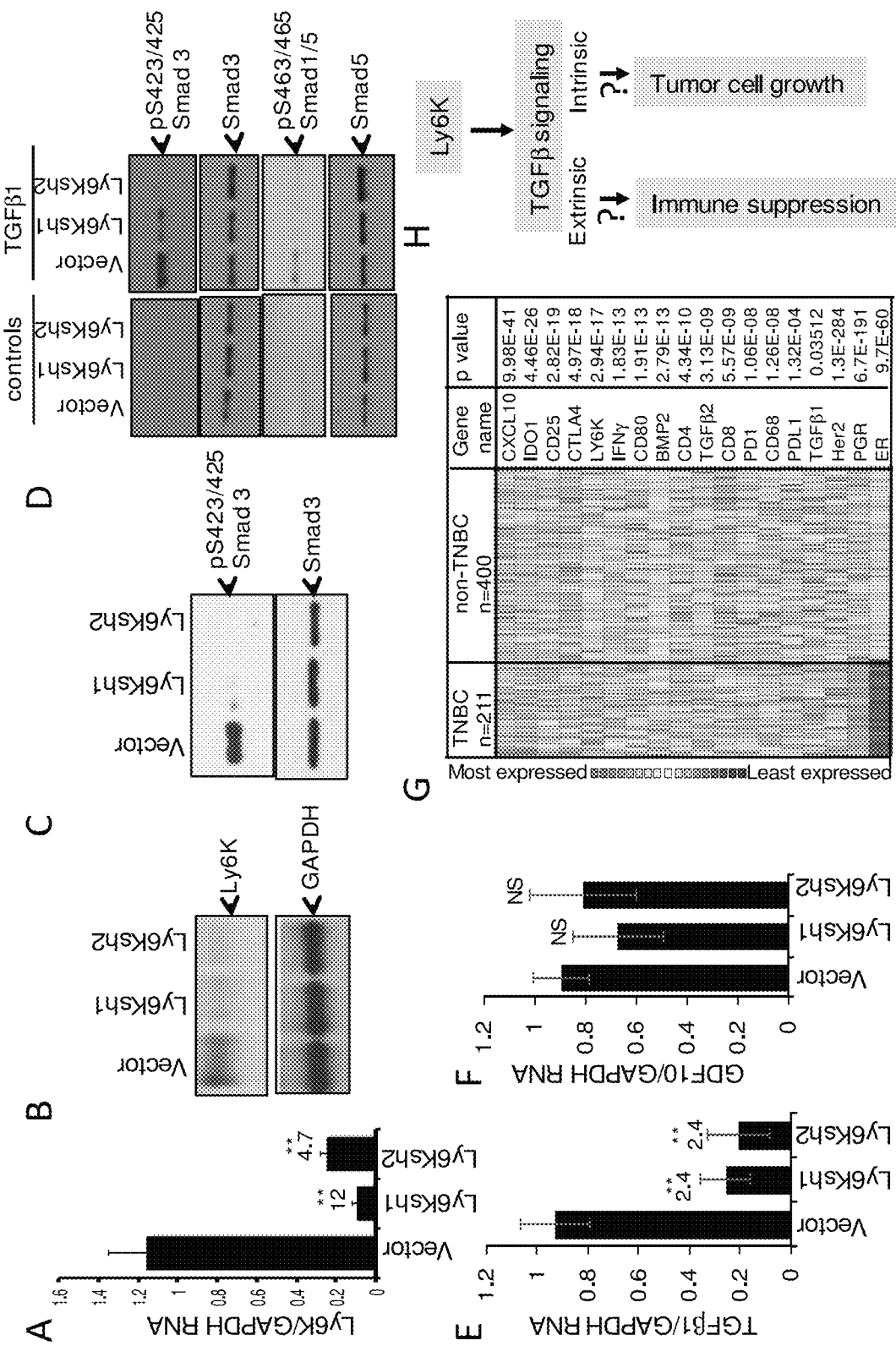
FIG. 2: Ly6K is required for TGFβ signaling. Lentiviral particles of shRNA against Ly6K (Ly6Ksh1, Ly6Ksh2) or non-targeting control shRNA (Vector) was stably transduced in MDA-MB-231[7]. (A) The qRT-PCR assay showing mRNA levels of Ly6K,  shows p<0.005, two tailed student T-test. (B) The western blot analysis for Ly6K. (C) Western blot analysis for phosphorylated and total Smad2/3 proteins. (D) Indicated cells were serum starved and stimulated with 10 ng/ml TGFβ1 for 30 min. Serum starved cells did not show detectable phosphorylate Smad protein. TGFβ1 stimulation for 30 min induced phosphorylated Smad2/3, Smad1/5. The qRT-PCR primers and antibodies are as described[7]. The qRT-PCR analysis using TaqMan gene expression assay for (E) TGFβ1, (F) GDF10 mRNA levels,  shows p<0.005, two tailed T-test. (G) Oncomine was used to assess the co-expression of mRNA levels of indicated genes in TNBC vs non-TNBC clinical cases using Curtis dataset[1]. n=number of patients. p-values indicate the p value within the row as calculated by Oncomine software. The most expressed genes are indicated with a red bar and the least expressed are indicated with a blue bar. (H) Ly6K may affect TGFβ signaling for tumor cell growth and increased immune suppression.

Increased TGFβ signaling is required for sustained tumor progression[6,18]. Intracellular TGFβ signaling induces epithelial to mesenchymal transition, increases cell cycle progression, proliferation, migration and therapeutic resistance in cancer cells[19-21]. Extracellular TGFβ signaling drives tumor immune escape by suppressing cytolytic function of T cells, expanding suppressive T-regulatory cells, inhibiting anti-tumor function of NK cells, inhibition of dendritic cell function and promotion of M2-type macrophages with pro-tumor activities[22-25]. TGF is a powerful immune suppressive cytokine, which is secreted in the tumor microenvironment by multiple cell type including cancer cells, and is associated with poor survival outcome in breast cancer[21,25-27]. We have previously shown in detail that Ly6K is required for endogenous or ligand-stimulated TGFβ/Smad signaling and epithelial to mesenchymal transition (EMT) in TNBC cells[9]. FIG. 2A-D summarize some of our key data[9] (FIG. 2A-D). Our new data indicate that Ly6K is upstream of transcriptional upregulation of TGF 1 ligand in cancer cells (FIG. 2E). Previously, we found that Ly6A/Sca-1 is required for transcriptional suppression of the tumor suppressor cytokine GDF10[28]; however, Ly6K did not affect expression of GDF10 mRNA (FIG. 2F). As summarized above, the current literature suggests a direct link between TGFβ signaling and cancer immune response. We therefore tested if Ly6K is correlated with immune-modulatory gene expression signatures in TNBC clinical cases. Oncomine analysis showed that Ly6K is significantly co-expressed with inflammatory cytokines TGFβ1/2, Bmp2, CXCL10, IFNγ; immunomodulatory proteins PD1, PDL1, CTLA4, CD80, CD25, IDO1 in TNBC vs Non-TNBC (FIG. 2G). The current literature also shows that TNBC has increased expression of genes associated with the immune escape of cancer cells[29]. It has been argued that these cases should respond better to immune therapy, however, TNBC cases have shown limited response against immune therapy thus far[2,30,31]. Anti-TGF 1 therapies have shown to induce tumor immune responses in the microenvironment and a direct effect on tumor cells[32]. Unfortunately, current therapeutics targeting TGFβ signaling focus on direct targeting of TGFβ receptors and/or Smad effector molecules, which may be the cause behind the severe side-effects arising due to probable loss of TGFβ signaling required for normal cell function[33-36]. Thus, there is a critical need for cancer specific anti-TGFβ1 therapies. We show here that the small molecule NSC243928 inhibits TGFβ signaling in a Ly6K dependent manner (described infra) in mouse tumor models including a humanized PDX model to investigate immune escape, inflammatory phenotype, tumor growth and TGFβ signaling in TNBC with increased Ly6K expression. By targeting Ly6K, the TGFβ associated immune suppression (extrinsic) and tumor cell growth (intrinsic) in TNBC (FIG. 2H) may be limited.

Ly6K is Required for Increased Immune Checkpoint Protein PD-L1 in Cancer Cells.

Figure 3:
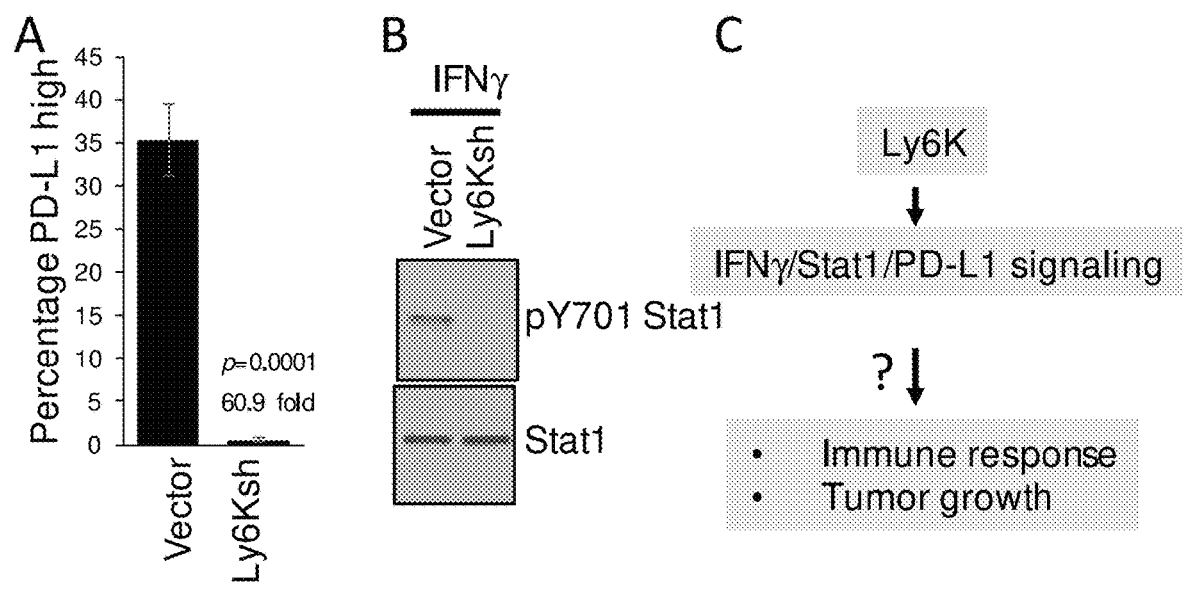
FIG. 3: Ly6K is required for IFNγ/PD-L1 pathway. (A) Indicated cells were serum starved prior to treatment with IFNγ 100 ng/ml overnight. Cells were labeled with anti-PD-L1 BV540 antibody or isotype control antibody prior to fixation to assess the cell surface expression of PD-L1 protein. Percentage of high PD-L1 cells were plotted in a bar graph from three different experiments and subjected to a two tailed student T-test, wherein p<0.05 is considered significant. (B) Western blotting analysis for indicated proteins. (C) Hypothesized effect of Ly6K on IFNγ/Stat1 pathway leading to increased PD-L1.

As shown in FIG. 2G, Ly6K is co-expressed with genes that inhibit the tumor immune response including PD-L1 ($5^{th}$ from the last row). PD-L1 is a protein highly expressed in cancer cells and plays an important role in deactivation of T-cell mediated cytotoxicity to cancer cells[5,37]. PD-L1 expression in cancer cells is regulated by multiple emerging pathways including IFNγ which is produced by T-cells and natural killer cells[38]. Phosphorylation of Stat1 by JAK kinases may be the major step in transcriptional activation of PD-L1 post IFNγ stimulation[39]. To explore the nature of Ly6K and PD-L1 co-expression, we treated control and Ly6K knockdown cells with IFNγ and assessed PD-L1 expression. We found that Ly6K knockdown led to reduced PD-L1 protein expression in IFNγ stimulated cells. No difference was seen in untreated cells[9] (FIG. 3A). We found that knockdown of Ly6K abolished Stat1 phosphorylation but did not affect total Stat1 protein levels (FIG. 3B). Accordingly, from these results, it seems that Ly6K induced cancer progression is at least partly due to its effect on PD-L1 expression and that the targeting of Ly6K by the small molecule NSC11150 will inhibit Ly6K-IFNγ/PD-L1 signaling. The role of Ly6K and its small molecule binder NSC11150 in PD-L1 mediated immune escape (FIG. 3C) will be further elucidated in the present disclosure.

Ly6K is Required for In Vivo Tumor Growth in Multiple Mouse Models.

Figure 4:
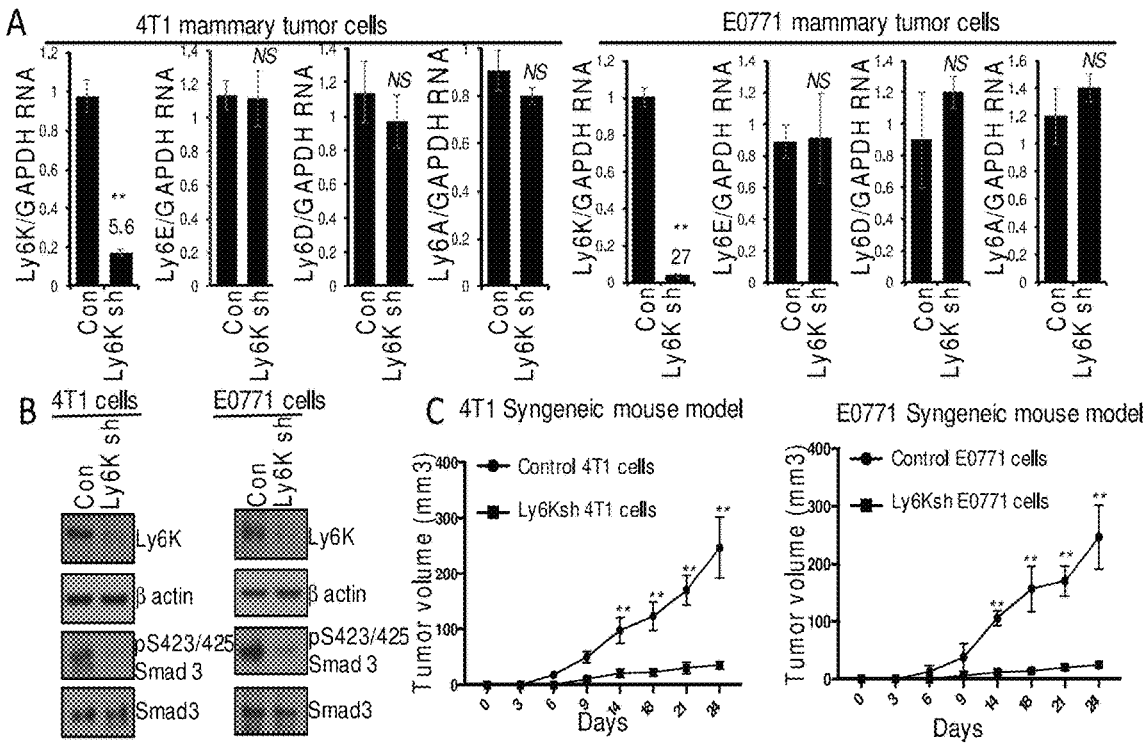
FIG. 4: Ly6K is required for tumor growth in syngeneic mammary tumor models. (A) The qRT-PCR analysis using TaqMAn gene expression assay for mRNA levels in scrambled shRNA (Con) and Ly6K knockdown (Ly6K sh) cells. (B) The western blot analysis (cell signaling antibodies). (C) For 4T1 model, 20K cells/site in Balb/c mice and for E0771, 500K cells/site in C57BL/6 syngeneic mice were transplanted into lower mammary fat pad by subcutaneous injection (number of mice 10 per cell line pair). Tumor measurements were performed using a Vernier caliper. The tumor volumes were calculated using equation ½*length*(width*width). ** indicates p<0.001 and NS=non-significant (p>0.05) in a two tailed student T-test.

We found that Ly6K expression is required for tumor progression in a xenograft tumor model of MDA-MB-231 in immune compromised nude mice[9]. Since nude mice have an impaired immune system, we decided to test the effect of Ly6K on tumor growth in the well-studied syngeneic mammary tumor mouse model using 4T1 (Balb/c origin) mice which is widely used to study immune associated tumor growth mechanisms and TGFβ signaling[40-42]. We used a second syngeneic mammary tumor model—E0771 (C57BL/6 origin), which is widely used in cancer immunotherapy research and TGFβ signaling[43,44]. We generated control and Ly6K knockdown 4T1 and E0771 cells using lentiviral non-targeting shRNA and mouse Ly6K shRNA. Ly6K knockdown cells showed significantly reduced mRNA levels of Ly6K compared to control cells. mRNA expression of mouse Ly6E, Ly6D and Ly6A (Sca-1) was not affected by the knockdown (FIG. 4A). Ly6K knockdown cells also showed significantly reduced protein levels of Ly6K. In addition, Ly6K knockdown cells showed loss of Smad2/3 phosphorylation (FIG. 4B). Ly6K knockdown cells did not give rise to isogenic tumor grafts (FIG. 4C). These results indicate that Ly6K may have a significant effect on non-immune and immune related mechanisms of tumor growth.

The Inhibition of Ly6K Signaling by Small Molecules is Feasible.

Figure 5:
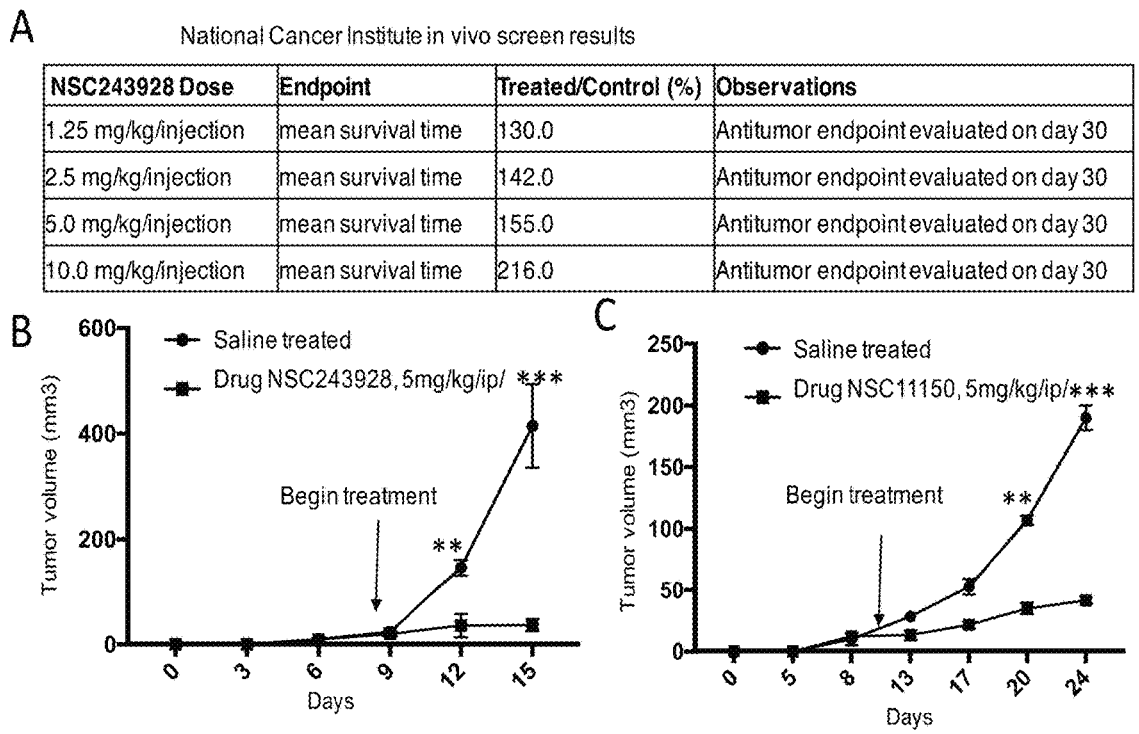
FIG. 5: Effect of small molecules on in vivo tumor growth. (A) NCI data-Indicated doses of NSC243928 in saline were given by intraperitoneal route (i.p.) every day for 9 days to BIDF syngeneic mice carrying L12 leukemia cells. Each group has 6 mice. Mouse were monitored for 30 days after drug treatment. Treat/control (%) indicate the therapeutic benefit. (B-C) 4T1 mice bearing 50-70 mm3 tumors were treated with NSC243928 (B) or NSC11150 (C) every second day with indicated doses in saline. The ** represents p<0.005 in a two tailed student T-test. Each group has 10 mice. Tumor measurements were done as shown in FIG. 4C.

We used surface plasmon resonance to identify small molecule binders of Ly6K. We screened a panel of 2000 small molecules, obtained from the Developmental Therapeutic Program (DTP, NCI). We discovered five small molecules that can bind specifically to Ly6K but did not show binding to Ly6E or Ly6D (KD range: 1 to 10 μM). These five molecules were further tested for their ability to induce cell death, TGFβ1/Smad2/3 phosphorylation, IFNγ/Stat1 phosphorylation and PD-L1 protein expression. NSC243928 and NSC11150 were selected for further study on the basis of specificity and selectivity in bio-assays and structural flexibility, which allow future modifications required for in-depth studies (described in FIG. 11). The small molecule NSC243928 has been previously used in an in vivo anti-tumor screen by the NCI on a L1210 leukemia model in BDF1 syngeneic mice, a standard model used between 1955 and 1975. The average survival in this tumor model is 2-3 weeks. Treatment with NSC243928 increased survival benefit from 30% to 100% in a dose dependent manner. The drug was not found to be toxic up to 10 mg/kg/i.p. treatment, however detailed data was not published (FIG. 5A). NSC11150 was not tested in in-vivo or in-vitro anti-tumor screens. Interestingly, NSC11150 has been used as an active ingredient in oral hygiene products as an anti-microbial and antibacterial agent (IDs: EP0693919, EP0696449). We surprisingly found that NSC243928 and NSC11150 (5 mg/kg/i.p. twice weekly after tumor establishment at 50-70 mm$^3$) can also suppress 4T1 mammary tumor growth in a syngeneic mouse model (FIG. 5B, C). As discussed infra, NSC243928 and NSC11150 inhibit TGFβ and PD-L1 pathways in a Ly6K dependent manner, indicating a mechanistic basic for the novel activities of these compounds (please see FIG. 11, 12). These experiments provide proof of the principle that small molecule targeting of Ly6K will have functional consequences and potentially lead to a better outcome in cancer treatment.

Ly6K plays an important role in increased TGFβ and PD-L1 signaling as shown here using TNBC cell lines, clinical samples, and syngeneic and xenograft tumor models. Its tissue-specific expression and its potent activation of tumor progression pathways makes it an attractive target for therapeutic intervention.

Accordingly, we have found that Ly6K, a cell surface protein with specific expression on cancer cells and normal cell expression limited to testis, is a novel biomarker that is associated with poor clinical outcome of breast, ovarian, lung, gastric, head and neck, bladder and colon cancer.

Ly6K is also found to be an enhancer of TGFβ and EMT pathways in cancer.

We also have surprisingly found novel activity for a molecule of known structure via binding of Ly6K to inhibit TGFβ signaling, as well as novel activity for a molecule of known structure via binding of Ly6K to inhibit immune checkpoint protein PD-L1.

Therefore, the present disclosure defines novel therapeutic targets for anti-TGFβ and inhibition of PD-L1 expression.

Figure 6:
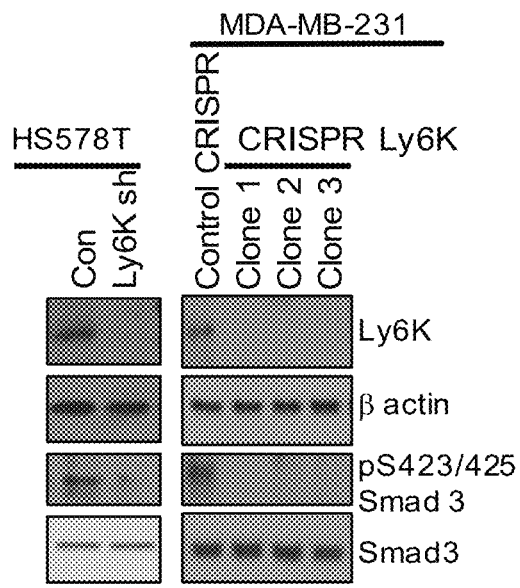
FIG. 6: Western blot (WB) analysis for indicated protein in Hs578t (left panel) (lentiviral shRNA for Ly6K (Ly6K sh) and non-targeting control shRNA (con)). For MDA-MB-231 (right panel), a Ly6K CRISPR/Cas9 plasmid and control CRISPR/Cas9 (Santa cruz, cat #sc404264, sc-418922 respectively) was according to manufacturer's instructions. Three clones were analyzed by WB.

TNBC Cell Lines:

Triple Negative Breast Cancer ("TNBC") cell lines have been assigned to distinct TNBC subtypes based on their gene expression signature[10]. All tested TNBC cell lines showed increased expression of Ly6K[9]. The mesenchymal, basal, and immunomodulatory TNBC subtypes have the highest Ly6K expression. We have successfully generated stable Ly6K knockdown cells using shRNA lentiviral technology in TNBC cells in MDA-MB-231 cells[9] and used the same method to generate control and Ly6K knockdown HS578t Ly6K knockdown cells (FIG. 6, left panel). We have developed and validated three Ly6K CRISPR clones from MDA-MB-231 cells (FIG. 6, right panel). DNA deletion of Ly6K via CRISPR resulted in loss of phosphorylation of Smad2/3 (FIG. 6).

Without wishing to be bound by theory, it appears that Ly6K increases tumor progression and suppression of immune surveillance by enhancing TGFβ signaling in TNBC.

Figure 7:
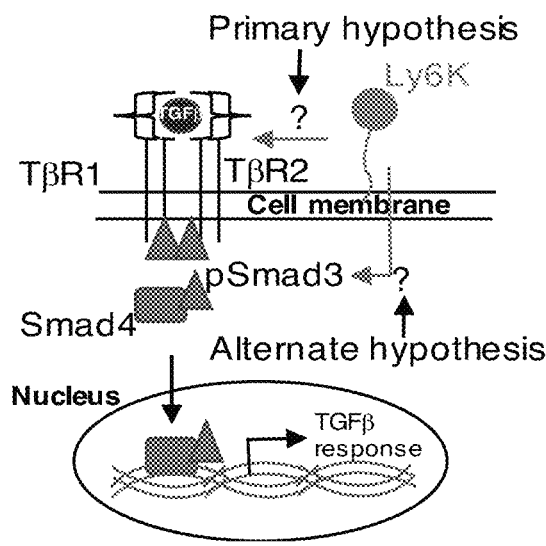
FIG. 7: Ly6K may interact with TGFβ receptor complex and stabilize it further to induce phosphorylation of Smad2/3.

Effect of Ly6K on Formation of TGFβ Receptor Complex:

Ly6K is required for endogenous and TGFβ1 ligand stimulated Smad2/3 phosphorylation (FIG. 7). Upon activation by their ligand, TGFβ receptor I (TβRI) and TGFβ receptor II (TORII) can form a complex and in turn induce phosphorylation of Smad2/3. Phosphorylated Smad2/3 protein can bind to Smad4 and subsequently translocate to the nucleus to induce transcription of TGFβ responsive genes.

Figure 8:
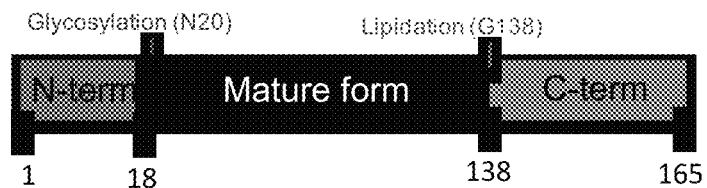
FIG. 8: Protein structure of Ly6K (UniProt.org).

Glycosylation and Lipidation of Ly6K Mediated TGFβ1 Signaling:

The 1-17 amino acid residues on N-terminus and C-terminus residues 139-141 are cleaved to form a mature Ly6K protein. The mature Ly6K protein of 18-138 residues have a glycosylation (N20) and lipidation (G138) site (FIG. 8). The glycosylation and lipidation are important post translation modification which are shown to be important for protein function and are often altered in tumorigenesis[45-49].

Figure 9:
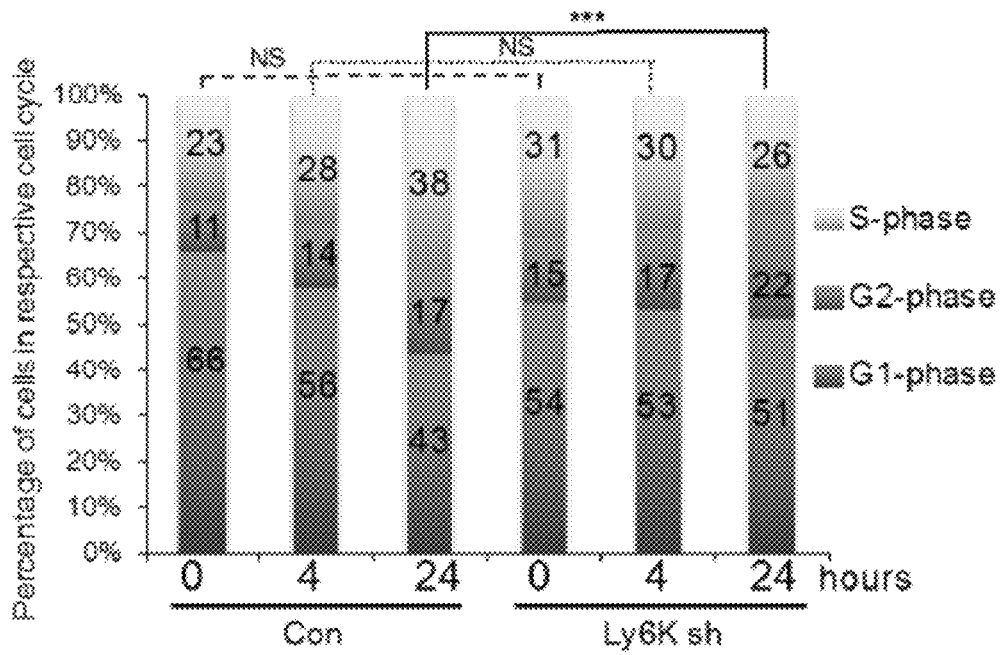
FIG. 9: Effect of Ly6K on cell cycle. Indicated cells were serum starved for overnight. Cells were then stimulated with 10% serum medium for 4 or 24 hours. Untreated cells were collected at the end of serum starvation (0 hour). PI labeling was performed for flow cytometry cell cycle analysis. Percentage of cells is indicated in the colored box (from top to bottom for each time point: S-phase, G2-phase, G1-phase). Graph represents one of the three independent experiments. Two tailed student T-test, p<0.005 significant, p>0.05 Non-significant (NS).

Ly6K/TGFβ Axis and its Effect on Tumor Cell Growth:

TGFβ has multiple effects on the progression of cancer cells including cell cycle checkpoint regulation, G1/S transition, apoptosis and autophagy[51,52] We found that Ly6K is required for G1/S transition post serum starvation (G0/G1 block). Control cells showed a steady decrease in the percentage of cells in G1-phase and an increase in S-phase cells. Ly6K knockdown cells showed stagnant G1- and S-phase cells (FIG. 9).

Figure 10:
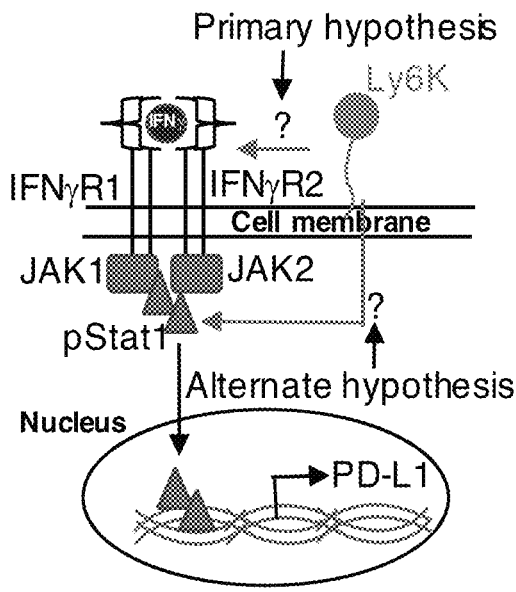
FIG. 10: Role of Ly6K in IFNγ pathway.
Figure 11A:
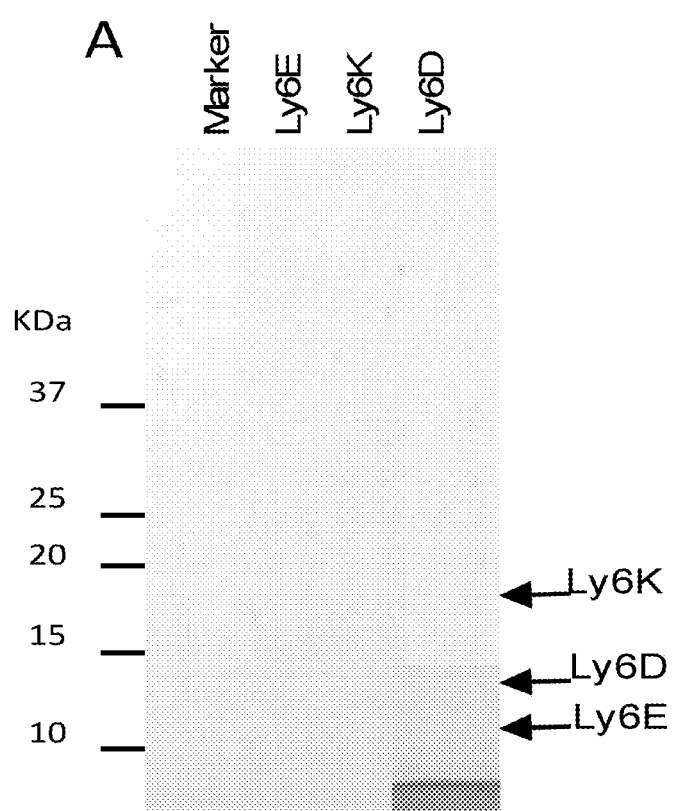
FIG. 11: Small molecule binders of Ly6K. (A) Mature form of Ly6E, Ly6D and Ly6K were cloned in pET24a N-term His tag vector (Epoch Biosciences); expressed in BL21DE *E. coli*; purified recombinant protein was prepared using histidine column in using a batch purification method and eluted in 500 mM imidazole PBS, dialyzed in PBS. 5 µl of eluate was run on the 15% SDS-PAGE showing the purity with expected size protein of single band. (B) Structure of NSC243928. (G) Structure of NSC11150. (C-F; H-K) Representative surface plasmon resonance (SPR) sensorgrams show time on X-axis and SPR binding response on Y-axis. Ly6K shows binding response in dose dependent manner to NSC243928 (C) and NSC11150 (H). Ly6E (E, J) and Ly6D (F, K) don't show binding response to NSC243928 and NSC11150; (D) shows the steady state response values (black dots) plotted vs the compound concentration and simple non-linear hyperbolic fit (red line) to the experimental data to determine KD values, KD value for NSC243928 binding to Ly6K is 1.9 M±0.5, $Chi^2$ T-test, p=0.00365. The corresponding data for NSC11150 are shown in corresponding lower panel. (I) KD of NSC11150 for Ly6K=1.6 µM±0.5, $Chi^2$ T-test, p=0.00507.
Figure 11B:
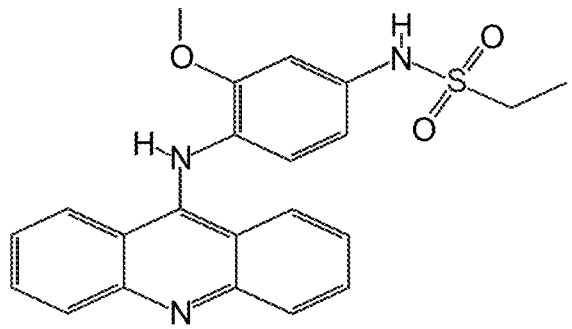
Figure 11C:
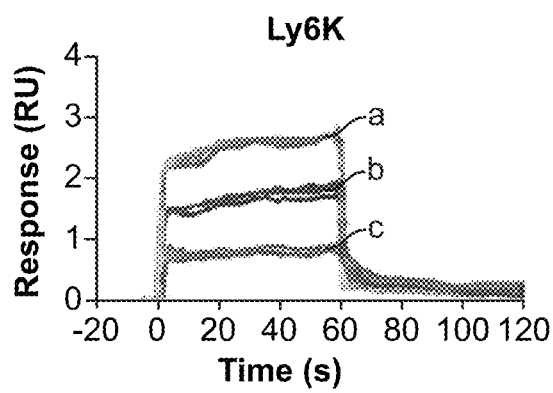
Figure 11D:
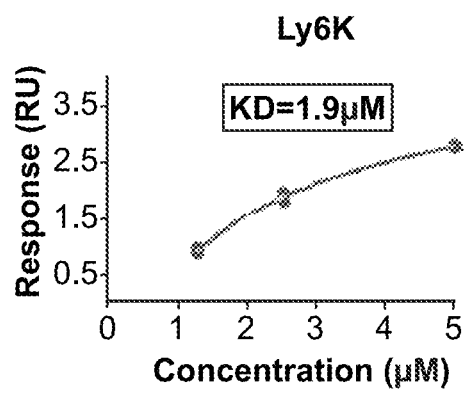
Figure 11E:
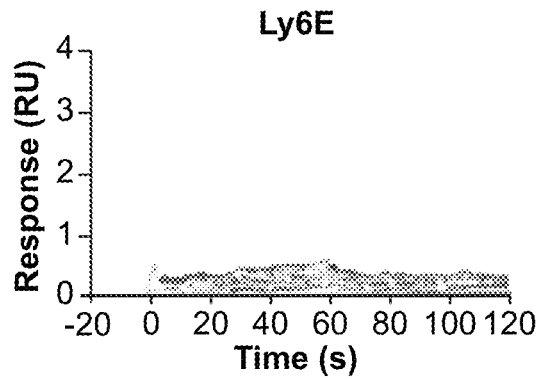
Figure 11F:
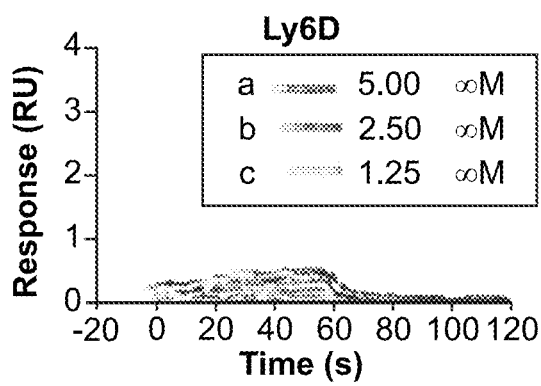
Figure 11G:
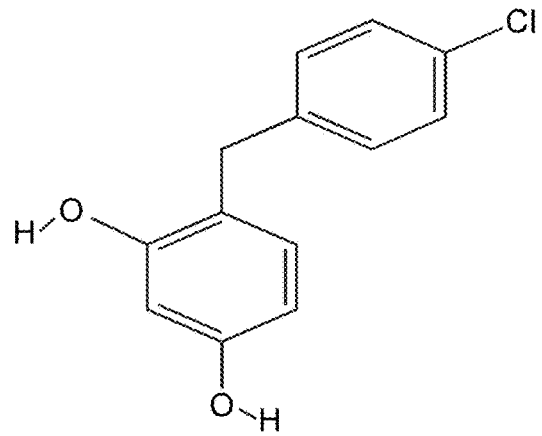
Figure 11H:
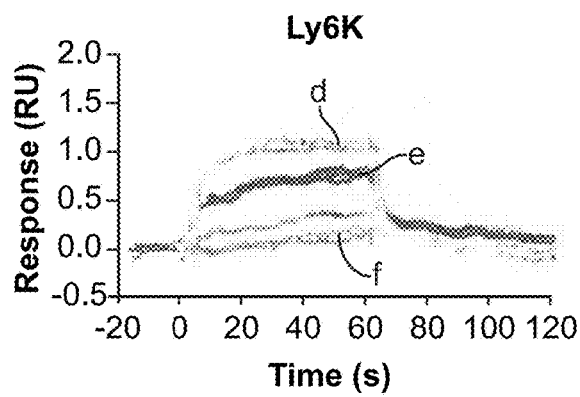
Figure 11I:
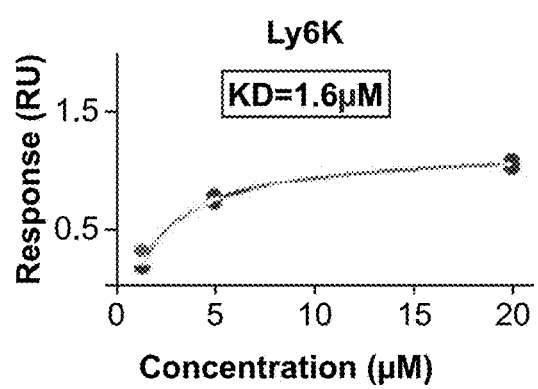
Figure 11J:
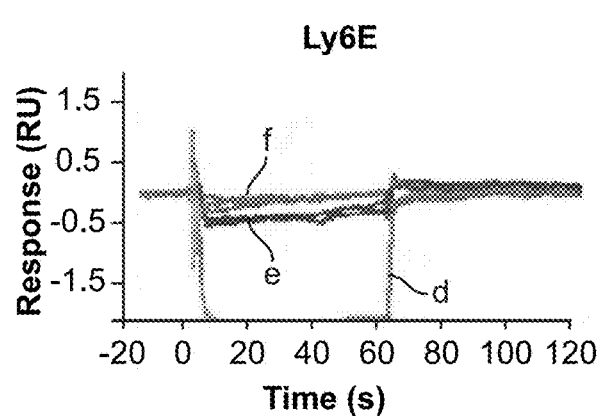
Figure 11K:
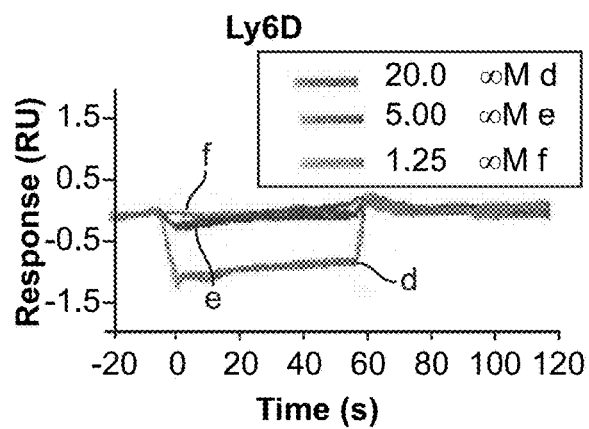

Ly6K in the IFNγ Pathway:

Ly6K is required for IFNγ-induced Stat1/3 phosphorylation and PD-L1 mRNA and protein expression in TNBC cells (FIG. 10). IFNγ is secreted by T-cells and it increases PD-L1 expression in cancer cells and macrophages[54,55]. IFNγ binds to IFNγ receptor 1(IFNγR1) inducing its dimerization, the dimerized IFNγR1 can than associate with dimerized IFNγRII. The complex then allows JAK1 and JAK2 activation, leading to an exposed Stat1 docking site in the intracellular space. Tyrosine phosphorylated Stat1 dissociates from this complex to form a homodimer which translocates into the nucleus to induce transcription of IFNγ responsive genes such as PD-L1[4 56].

Effect of Ly6K on Stabilization of IFNγ Receptor Levels:

Ly6K is a GPI anchored protein and located on the cell surface. This class of proteins may concentrate in lipid rafts that are involved in receptor-mediated signal transduction pathways and membrane trafficking[12,13]. Ly6K may be required for adequate localization of IFNγR1/2 on the cell surface.

Ly6K in IFNγ Induced PD-L1 Expression:

Ly6K in cancer cells may engage with alternative pathways to increase IFNγ-induced PD-L1 expression, which may circumvent classical signaling cascades of IFNγ binding to IFNγR1/2 followed by Stat3 phosphorylation.

Ly6K Modification and its Role in IFNγ Signaling:

Ly6K at the cell surface may be required for stability of the IFNγ receptor complex and phosphorylation of Stat1, which results in increased expression of PD-L1.

The Effect of Small Molecule Binders of Ly6K in Tumor Regression:

We performed a surface plasmon resonance assay using the Biacore T100 by immobilizing the purified human Ly6K protein on the surface of a CM5 chip and screening the binding with a small molecule library containing 2000 compounds (Developmental Therapeutics Program, NCI). An initial screening of molecules was performed at 1 or 10 µM compound, based on solubility. We used a model that compares the actual binding maximum (RUactual) with the theoretical binding maximum (RUtheor). A ratio of RUactual to RUtheor between 0.9-1.0 suggests binding, and the corresponding compound was considered a 'hit'. Hits (RUactual to RUtheor of 0.7-2.0) were then reviewed by a team of medicinal chemists and those with structural potential were selected for further study. Selected molecules were tested for binding with other members of the Ly6 family, namely Ly6E and Ly6D. Five of the selected compound showed specific binding to Ly6K. We have selected NSC1150 for further analysis as a lead hit compound due its structure which was suitable for structural modification required for tagging and further improving the compound. See FIGS. 11A-K.

Ly6K Binding Small Molecule Interferes with Ly6K/TGFβ and Ly6K/IFNγ Signaling.

Figure 12:
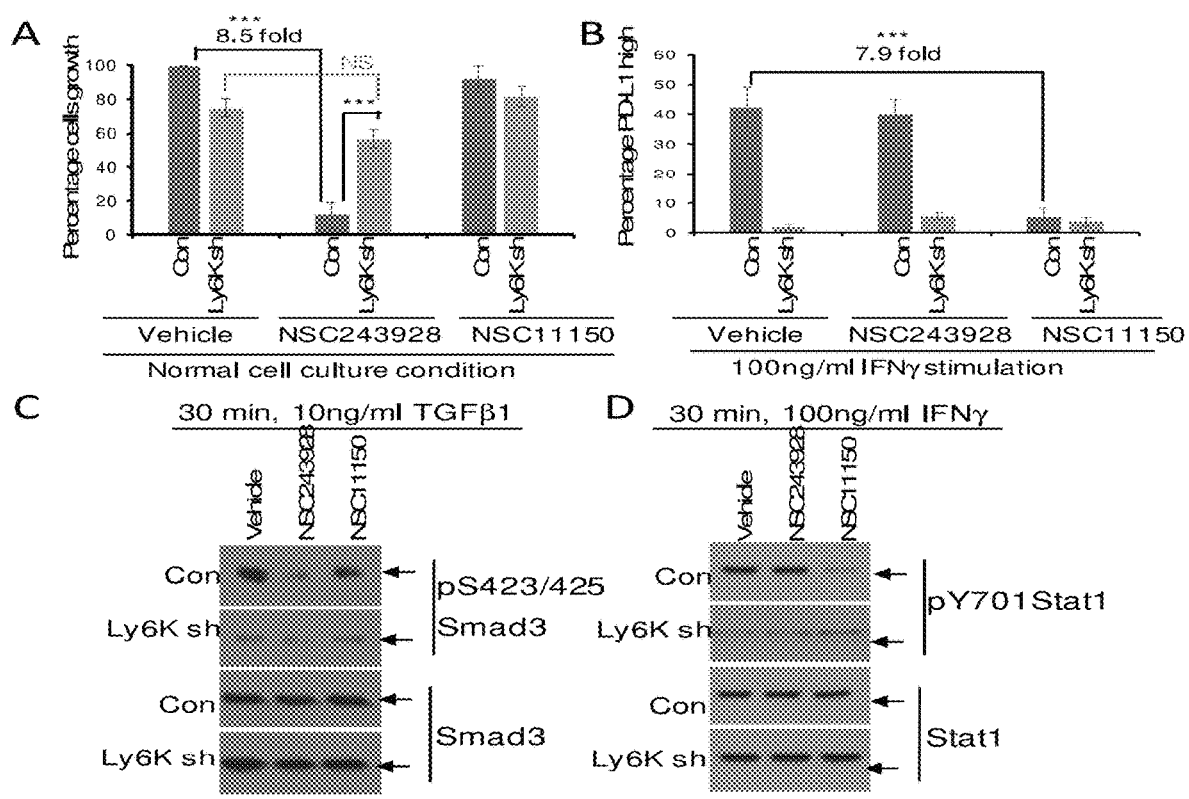
FIG. 12: Effect of small molecule binders of Ly6K. (A) Indicated cells were seeded and allowed to attach overnight, then treated with 2 µM drugs for 72 hours. Cell titer assay was performed to measure cell growth. (B) Cells were serum starved and treated with 100 ng/ml IFNγ with 2 µM drugs. PD-L1 was measure in live cells (using a zombie live-dead stain) as described in FIG. 3A. The graph was plotted from three experiments. (C, D) Indicated cells were allowed to attach, serum starved overnight and then treated with TGFβ (C) or IFNγ (D) in the presence of 2 µM drug for 30 minutes and western blot analysis was performed. The *** represents p<0.0005 and NS=non-significant in a two-tailed student T-test.

NSC243928 diminished the growth of control MDA-MB-231 cells but lost its activity in Ly6K knockdown cells. NSC11150 did not show significant effect on cell death at 2 µM (FIG. 12A). NSC11150 induced cell death at 100 µM in both control and Ly6K knockdown cells (not shown). Treatment with NSC11150 led to inhibition of PD-L1 expression in control cells, while NSC243928 did not show significant effect of PD-L1 protein expression (FIG. 12B). NSC243928 inhibited the TGFβ1 induced phosphorylation of Smad2/3; NSC11150 had no effect on TGFβ1/Smad2/3 signaling (FIG. 12C). NSC11150 inhibited IFNγ induced phosphorylation of Stat1; NSC243928 had no effect on IFNγ/Stat1 signaling (FIG. 12D). These data suggest that we have identified a novel activity of NSC243928 in cell growth, TGFβ1/Smad2/3 signaling and of NSC11150 in PD-L1 protein expression and IFNγ/Stat1 signaling.

NSC243928 and NSC11150 have Distinct Binding Pockets on Ly6K.

Figure 13:
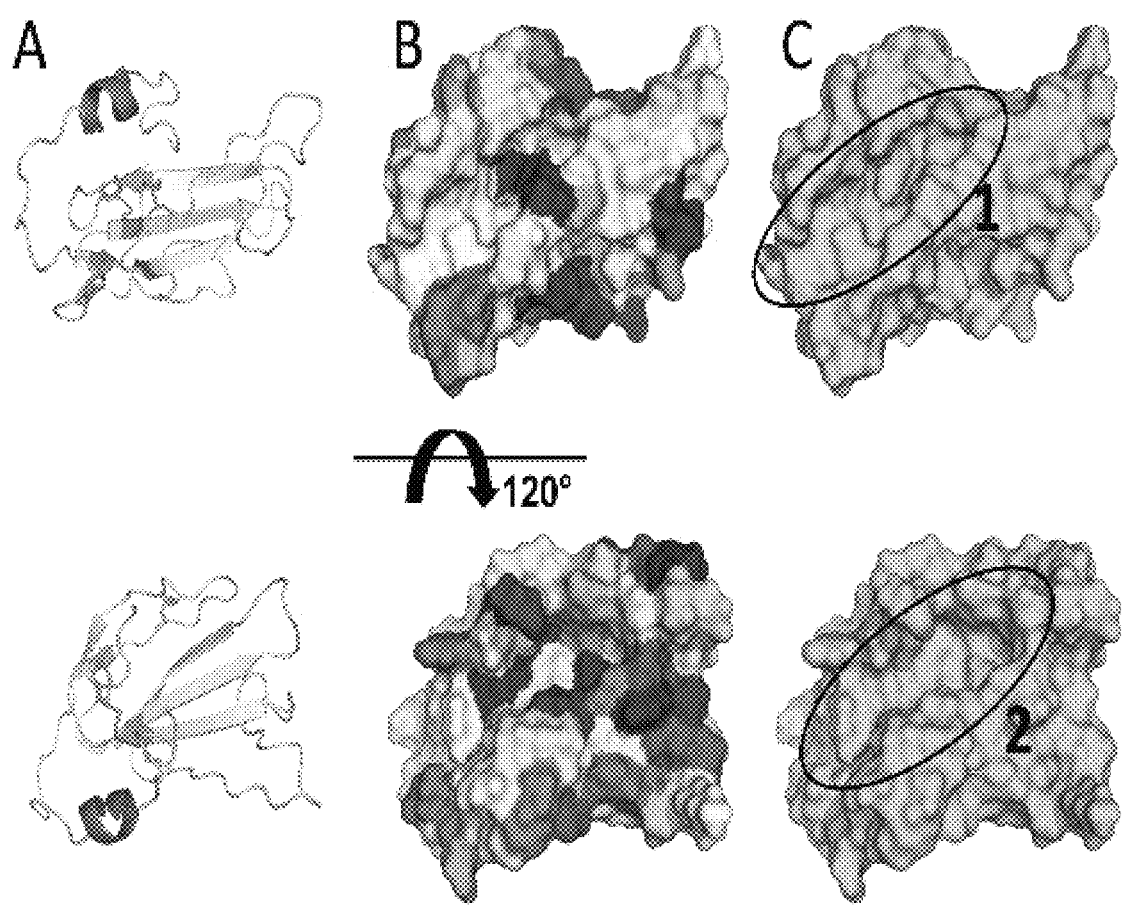
FIG. 13: Homology modeling of Ly6K mature protein. (A) backbone of the protein, (B) surface view with amino acids conservation in Ly6 family of proteins (blue—conserved residues, red-variable residues), (C) binding site 1 near the N-terminus. The corresponding 120° rotation reveals binding site 2 in proximity to the C-terminus 5 of the Ly6K.
Figure 14:
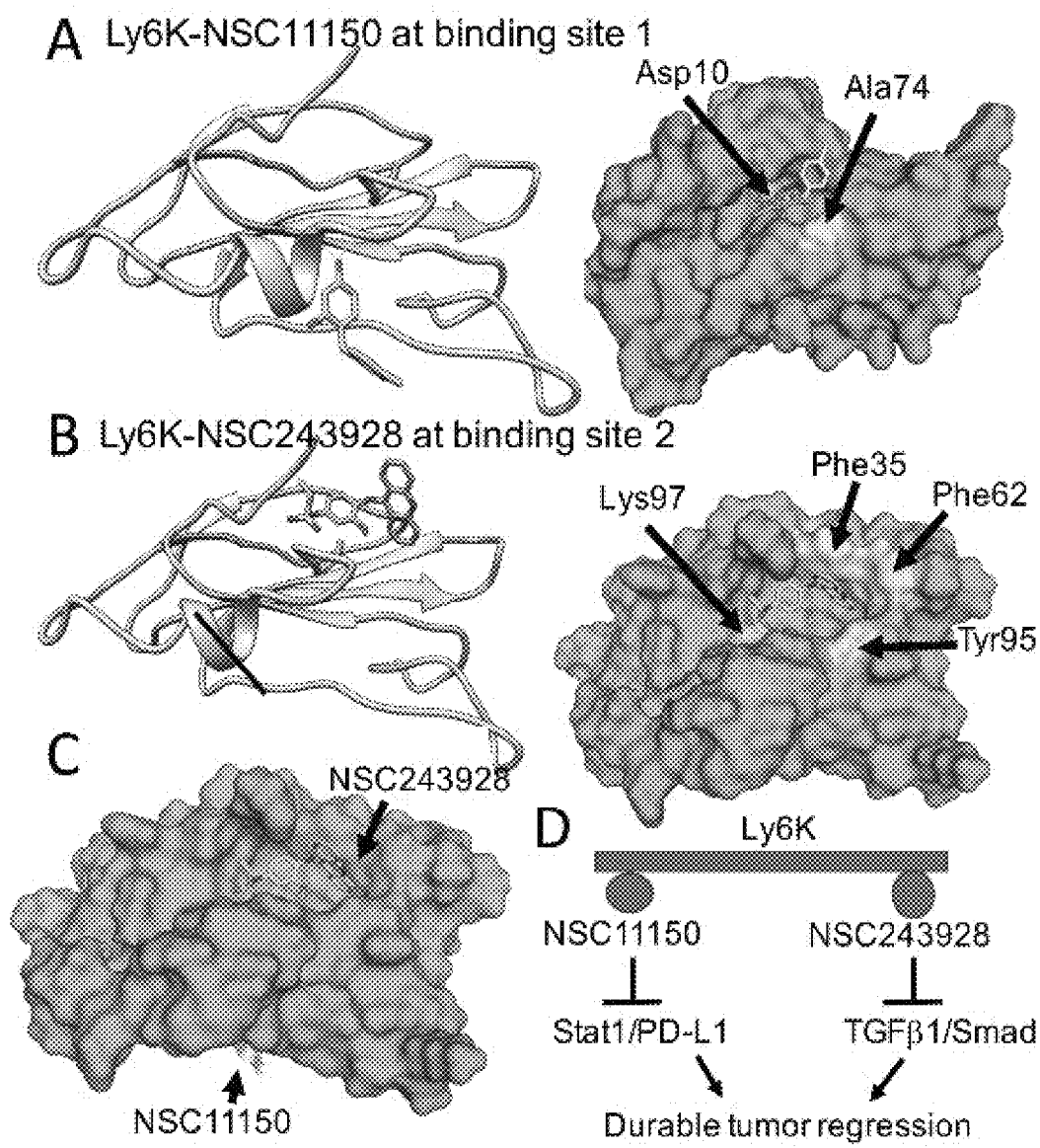
FIG. 14: Mechanisms of small molecule binders of Ly6K. (A-B) Ly6K binding to NSC11150 binding on site 1 (A) and Ly6K binding to NSC243928 binding on site 2 (B) shown in the ribbon (left panels) and surface models (right panels). Binding prediction using Swiss dock. The amino acid identity involved in binding is indicated. (C) Surface view showing both molecules' binding to Ly6K. (D) Our working hypothesis is that Ly6K may be targeted via two structurally distinct molecules to regulate immune checkpoint proteins and TGFβ signaling.

The homology modeling of human Ly6K protein (Uniprot id-Q17RY6) was performed using I-TASSER and the structure of human LYNX1 (PDB code: 2L03) as a template[57]. The residues 1-121 of LYNX1 correspond to residues 18-138, which constitute the mature form of Ly6K. The best Ly6K model with a C score of −1.62, estimated TM score of 0.52±0.150 was modified, as we omitted 12 amino acids on the C-terminal due to steric clashes. The Lys6K model including residues 18-126 was used for docking studies. The docking of NSC243928 and NSC11150 to the Ly6K model was performed with SwissDock[58] using 'automatic mode' to identify the potential binding pockets. This modeling revealed two potential binding sites on the Ly6K protein. See FIGS. 13A-C. Approximately 10% of the best predicted poses as judged by the 'FullFitness' parameter for NSC11150 corresponded to binding site 1. At the same time ~5% of best poses for NSC243928 corresponded to binding site 2. See FIGS. 14A-D.

Determination of the Maximum Tolerated Dose (MTD) for NSC243928 and NSC11150:

Inpreliminary experiments, we saw a therapeutic benefit at 5 mg/kg/ip dose with no visible toxicity for NSC243928 and NSC11150.

Example 2—Evaluation of the Binding Interaction Between the Small Molecule Inhibitors and Ly6K The binding interaction between Ly6K and small molecule inhibitor NSC243928 was evaluated. As shown in FIG. 15, hydrophobic contacts seem to play the most important role in interactions between NSC243928 and Ly6K. The acridinylamino group form extensive contacts with side chains of Phe35, Phe62, Val64 and Tyr95. At the same time side chain of Ile52 and Ala54 are predicted to be in the vicinity of the phenyl group. Our model also suggest that Asp1 and Lys97 are potential candidates to participate in interactions with the sulfoanilide moiety.

The binding interaction between Ly6K and small molecule inhibitor NSC11150 was also evaluated. As shown in FIG. 16, hydroxyl group attached to carbon 1 participates in two hydrogen bonds. The first hydrogen bond is formed between the compound and oxygen from side chain carboxyl group of Asp10, the second hydrogen bond involves nitrogen atom from the main chain of Cys98. There are several amino acids that form close contact with NSC11150. For example, Asn3, Gln8, Pro11, Ala74 and Glu76 form a part of binding site 1 that provides most of the interactions.

Figure 17:
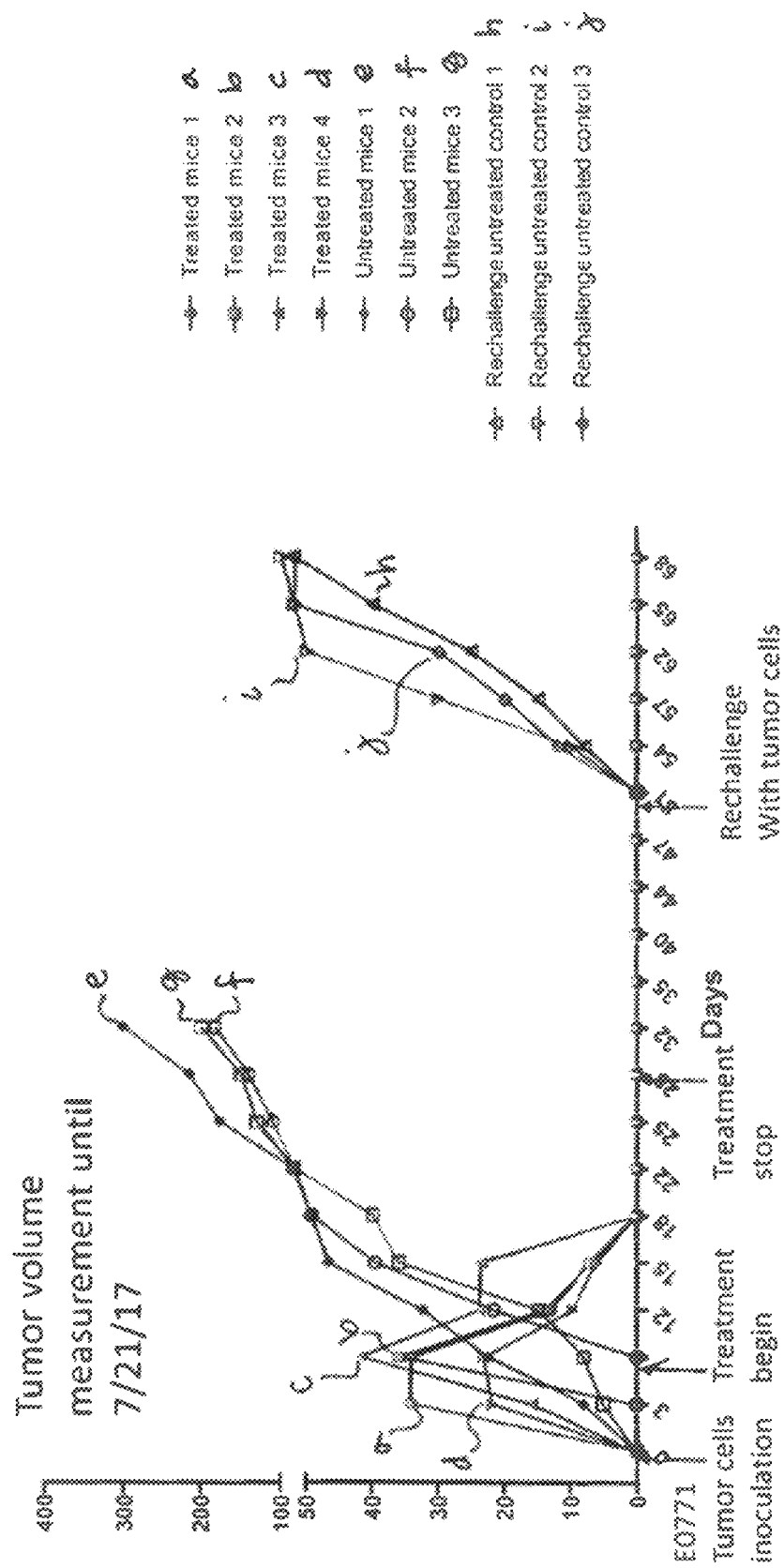
FIG. 17: Ly6K binding small molecules induce immunity against tumor growth. Treatment of E0771 tumors in a syngeneic C57Bl/6 model with individual small molecules reduced tumor growth, while combination treatment with the two small molecules completely eliminated tumor growth. The treatment was halted after tumor disappearance. Three weeks later, the cured mice were re-challenged with E0771 cells, with complete, durable protection against tumor growth.

Example 3—Small Molecule Binders of Ly6K Inhibit Tumorigenic Growth and Induce Immunity We have previously shown that members of the Ly6 gene family, namely Ly6E, Ly6D, Ly6H and Ly6K are expressed in multiple types of solid human cancers and that the increased expression of these genes is associated with poor outcome (Luo et al., *Oncotarget* 7(10):11165-93 (2016), which is hereby incorporated by reference in its entirety). We also have found that Ly6K and Ly6E are required for in vivo tumor growth and anti-tumor immune response (Al Hossiny et al., *Cancer Res.* 76(11):3376-86 (2016), which is hereby incorporated by reference in its entirety). Ly6K is an attractive target due to its cancer cell-specific expression; normal organ expression of Ly6K is limited to testis. We used surface plasmon resonance technology to identify two small molecule binders of Ly6K. These molecules showed strong binding to Ly6K (kd range 1-2 µM) but not to Ly6E and Ly6D. Combined small molecule treatment led to reduced TGFβ signaling and reduced PDL1 expression in MDA-MB-231 cells. Homology modeling showed that the two small molecules bind to the N-terminus and C-terminus of the mature Ly6K protein, respectively. Treatment of E0771 tumors in a syngeneic C57Bl/6 model with individual small molecules reduced tumor growth, while combination treatment with the two small molecules completely eliminated tumor growth (FIG. 17). The treatment was halted after tumor disappearance. Three weeks later, the cured mice were re-challenged with E0771 cells, with complete, durable protection against tumor growth. These results suggest that Ly6K inhibitors have anti-tumor properties and induce host-protective anti-tumor immunity. Our data implicate the novel biomarker Ly6K as a therapeutic target and immune modulator in multiple tumor types with high expression of Ly6K.

REFERENCES

1. Lehmann & Pietenpol, *Breast* 24 Suppl 2, S36-40 (2015).
2. Nanda et al., *Journal of Clinical Oncology* 34, 2460-2467 (2016).
3. Amirikia et al., *Cancer* 117, 2747-2753 (2011).

4. Abiko et al., *British Journal of Cancer* 112, 1501-1509 (2015).
5. Soliman et al., *PLoS ONE* 9, e88557 (2014).
6. Ikushima & Miyazono, *Nature Reviews Cancer* 10, 415-424 (2010).
7. Saunier & Akhurst, *CCDT* 6, 565-578 (2006).
8. Luo et al., *Oncotarget* 7, 11165-11193 (2016).
9. AlHossiny et al., *Cancer Res* 76, 3376-3386 (2016).
10. Lehmann et al., *J Clin Invest* 121, 2750-2767 (2011).
11. Uhlen, *Molecular &Cellular Proteomics* 4, 1920-1932 (2005).
12. Uhlen et al., *Science* 347, 1260419-1260419 (2015).
13. Loughner et al., *Human Genomics* 201610:1 10, 10 (2016).
14. Yoshitake et al., *Biochem. Biophys. Res. Commun.* 372, 277-282 (2008).
15. Matsuda et al., *British Journal of Cancer* 104, 376-386 (2011).
16. Ishikawa et al., *Cancer Res* 67, 11601-11611 (2007).
17. Matsuda et al., Abstract 1152, *J. Urology* 181(4, Suppl.): 410-11 (2009).
18. Buck & Knabbe, *Ann. New YorkAcad. Sci.* 1089, 119-126 (2006).
19. Katsuno et al., *Current Opinion in Oncology* 25, 76-84 (2013).
20. Ding et al., *Oncology Letters* 11, 4040-4044 (2016).
21. Desruisseau et al., *British Journal of Cancer* 94, 239-246 (2006).
22. Yoshimura. & Muto, in *Negative Co-Receptors and Ligands* 350, 127-147 (2010).
23. Wilson et al., *PLoS ONE* 6, e22842 (2011).
24. Zhang et al., *Oncotarget* 7, 52294-52306 (2016).
25. Li et al., *Immunity* 26, 579-591 (2007).
26. Grotendorst et al., *Journal of Cellular Physiology* 140, 396-402 (1989).
27. Barcellos-Hoff & Akhurst, *Breast Cancer Research* 2009 11:1 11, 202 (2009).
28. Upadhyay et al., *Proc. Natl. Acad. Sci. U.S.A.* 108, 7820-7825 (2011).
29. Garcia-Teijido et al., *Clinical Medicine Insights. Oncology* 10, 31-39 (2016).
30. Stagg & Allard, *Therapeutic Advances in Medical Oncology* 5, 169-181 (2013).
31. Gandini et al., *Critical Reviews in Oncology/Hematology* 100, 88-98 (2016).
32. Neuzillet et al., *Pharmacology & Therapeutics* 147, 22-31 (2015).
33. Bierie & Moses, *Nature Reviews Cancer* 6, 506-520 (2006).
34. Yingling et al., *Nature Reviews Drug Discovery* 3, 1011-1022 (2004).
35. Smith et al., *Clin Cancer Res* 18, 4514-4521 (2012).
36. Connolly et al., *Int. J. Biol. Sci.* 8, 964-978 (2012).
37. Chen & Han, *J Clin Invest* 125, 3384-3391 (2015).
38. Gajewski et al., *Nat. Immunol.* 14, 1014-1022 (2013).
39. Garcia-Diaz et al., *Cell Reports* 19, 1189-1201 (2017).
40. Pulaski & Ostrand-Rosenberg, *Curr Protoc Immunol* Chapter 20, Unit 20.2-20.2.16 (2001).
41. Sato et al., *PLoS ONE* 10, e0126483 (2015).
42. Nam et al., *Cancer Res* 68, 3835-3843 (2008).
43. John et al., *Clin Cancer Res* 19, 5636-5646 (2013).
44. Cunha et al., *Cancer Res* 75, 2445-2456 (2015).
45. Resh, *Trends in Molecular Medicine* 18, 206-214 (2012).
46. Magee et al., *Pancreatology* 14, e4 (2014).
47. Phillips, *Nature Reviews Urology* (2014).
48. Couldrey & Green, *Breast Cancer Research* 2009 11:12, 321 (2000).
49. Bellis, *Biochimica et Biophysica Acta (BBA)—Biomembranes* 1663, 52-60 (2004).
50. Upadhyay et al., *Oncogene* 27, 5845-5855 (2008).
51. Kubisch et al., *Semin. Cancer Biol.* 23, 252-261 (2013).
52. Feng et al., *EMBO J.* 19, 5178-5193 (2000).
53. Ligaba et al., *PLoS ONE* 10, e0116755 (2015).
54. Lin et al., *J. Biomed. Sci.* 24, 10 (2017).
55. Schoenborn & Wilson, *Adv. Immunol.* 96, 41-101 (2007).
56. Concha-Benavente & Ferris, *J. ImmunoTherapy Cancer* 2014 2:3 2, P199 (2014).
57. Dai et al., *Molecular Therapy—Nucleic Acids* 5, e349 (2016).
58. Kang et al., *Oncotarget* (2015).
59. Kong et al., *Bioorganic Med. Chem.* 25, 2226-2233 (2017).
60. Minor et al., *Acta Crystallogr SectD Biol Crystallogr* 62, 859-866 (2006).
61. Cymborowski et al., *JStructFunct Genomics* 11, 211-221 (2010).
62. Emsley & Cowtan, *Acta Crystallogr SectD Biol Crystallogr* 60, 2126-2132 (2004).
63. Lovell et al., *Proteins* 50, 437-450 (2003).
64. Kirillova et al., *Acta Crystallogr SectD Biol Crystallogr* 63, 348-354 (2007).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for inhibiting Ly6K protein in a subject in need thereof, comprising administering to the subject:

(i) an effective amount of a compound of formula:

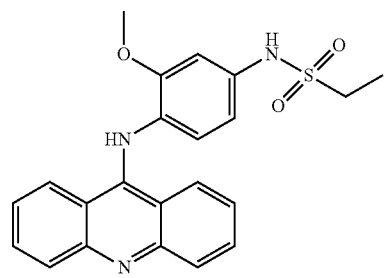 [SMILES: CCS(=O)(=O)Nc1ccc(Nc2c3ccccc3nc3ccccc23)c(OC)c1]

or a pharmaceutically acceptable salt thereof, or (ii) an effective amount of a compound of formula:

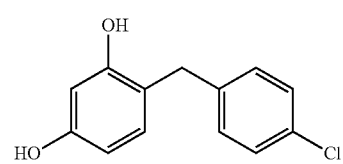

or a pharmaceutically acceptable salt thereof, or (iii) an effective amount of a compound of formula:

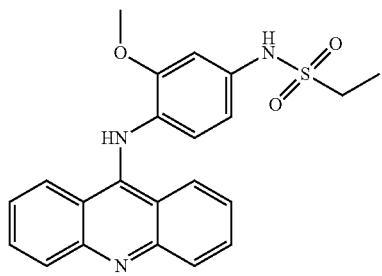 [SMILES: CCS(=O)(=O)Nc1ccc(Nc2c3ccccc3nc3ccccc23)c(OC)c1]

or a pharmaceutically acceptable salt thereof, and
an effective amount of a compound of formula:

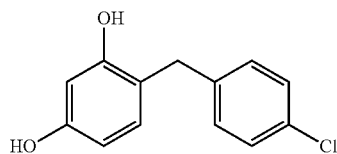 [SMILES: Oc1ccc(Cc2ccc(Cl)cc2)c(O)c1]

or a pharmaceutically acceptable salt thereof,
wherein the effective amount is sufficient to lower activity of the Ly6k protein in the subject.

2. The method of claim 1, comprising administering to the subject an effective amount of a compound of formula:

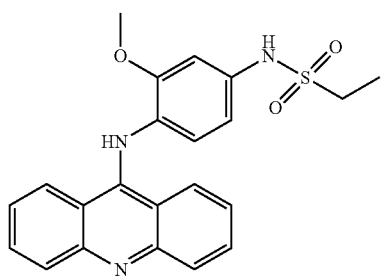 [SMILES: CCS(=O)(=O)Nc1ccc(Nc2c3ccccc3nc3ccccc23)c(OC)c1]

or a pharmaceutically acceptable salt thereof.

3. The method of claim 1, comprising administering to the subject an effective amount of a compound of formula:

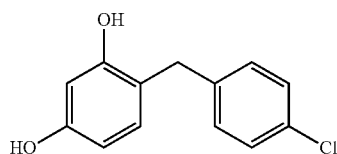 [SMILES: Oc1ccc(Cc2ccc(Cl)cc2)c(O)c1]

or a pharmaceutically acceptable salt thereof.

4. The method of claim 1, comprising administering to the subject:

an effective amount of a compound of formula:

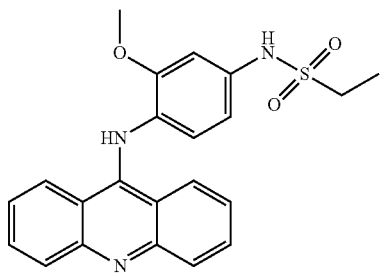 [SMILES: CCS(=O)(=O)Nc1ccc(Nc2c3ccccc3nc3ccccc23)c(OC)c1]

or a pharmaceutically acceptable salt thereof, and
an effective amount of a compound of formula:

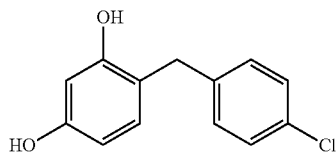 [SMILES: Oc1ccc(Cc2ccc(Cl)cc2)c(O)c1]

or a pharmaceutically acceptable salt thereof.

5. A method for treating a disorder mediated by Ly6K protein in a subject in need thereof, comprising administering to the subject:

(i) an effective amount of a compound of formula:

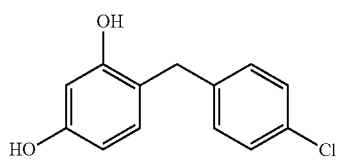 [SMILES: Oc1ccc(Cc2ccc(Cl)cc2)c(O)c1]

or a pharmaceutically acceptable salt thereof, or
(ii) an effective amount of a compound of formula:

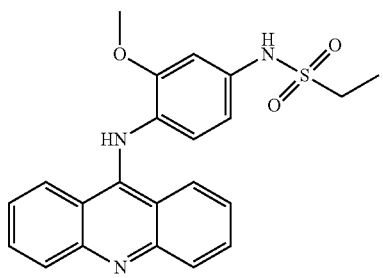 [SMILES: CCS(=O)(=O)Nc1ccc(Nc2c3ccccc3nc3ccccc23)c(OC)c1]

or a pharmaceutically acceptable salt thereof, and an effective amount of a compound of formula:

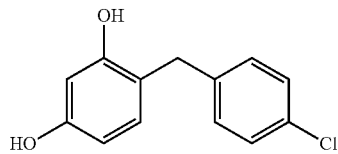 [SMILES: Oc1ccc(Cc2ccc(Cl)cc2)c(O)c1]

or a pharmaceutically acceptable salt thereof.

6. The method of claim 5, comprising administering to the subject an effective amount of a compound of formula:

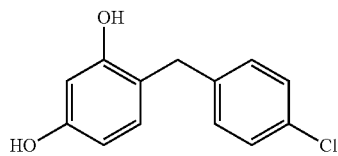 [SMILES: Oc1ccc(Cc2ccc(Cl)cc2)c(O)c1]

or a pharmaceutically acceptable salt thereof.

7. The method of claim 5, comprising administering to the subject an effective amount of a compound of formula:

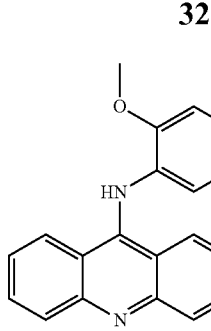

or a pharmaceutically acceptable salt thereof, and an effective amount of a compound of formula:

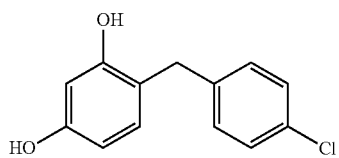 [SMILES: Oc1ccc(Cc2ccc(Cl)cc2)c(O)c1]

or a pharmaceutically acceptable salt thereof.

8. The method of claim 5, wherein the disorder is a triple negative breast cancer, mesenchymal breast cancer, basal breast cancer, or immunomodulatory breast cancer.

* * * * *